US011622965B2

(12) United States Patent
He

(10) Patent No.: US 11,622,965 B2
(45) Date of Patent: Apr. 11, 2023

(54) METHODS FOR TREATING LYMPHOID MALIGNANCIES

(71) Applicant: ZHEJIANG DTRM BIOPHARMA CO. LTD., Hangzhou (CN)

(72) Inventor: Wei He, Audubon, PA (US)

(73) Assignee: ZHEJIANG DTRM BIOPHARMA CO. LTD., Hangzhou (CN)

( * ) Notice: Subject to any disclaimer, the term of this patent is extended or adjusted under 35 U.S.C. 154(b) by 77 days.

(21) Appl. No.: 16/763,483

(22) PCT Filed: Oct. 26, 2018

(86) PCT No.: PCT/US2018/057660
§ 371 (c)(1),
(2) Date: May 12, 2020

(87) PCT Pub. No.: WO2019/084369
PCT Pub. Date: May 2, 2019

(65) Prior Publication Data
US 2020/0289517 A1    Sep. 17, 2020

Related U.S. Application Data

(60) Provisional application No. 62/578,081, filed on Oct. 27, 2017.

(51) Int. Cl.
| | | |
|---|---|---|
| *A61K 31/519* | (2006.01) | |
| *A61K 31/436* | (2006.01) | |
| *A61K 31/4439* | (2006.01) | |
| *A61P 35/02* | (2006.01) | |
| *A61K 9/20* | (2006.01) | |
| *A61K 9/48* | (2006.01) | |
| *A61K 35/17* | (2015.01) | |
| *A61K 45/06* | (2006.01) | |
| *C07K 16/28* | (2006.01) | |

(52) U.S. Cl.
CPC .......... *A61K 31/519* (2013.01); *A61K 31/436* (2013.01); *A61K 31/4439* (2013.01); *A61P 35/02* (2018.01); *A61K 9/20* (2013.01); *A61K 9/48* (2013.01); *A61K 35/17* (2013.01); *A61K 45/06* (2013.01); *C07K 16/2878* (2013.01); *C07K 16/2887* (2013.01); *C07K 16/2893* (2013.01)

(58) Field of Classification Search
CPC ............... A61K 31/519; A61K 31/436; A61K 31/4439; A61K 9/20; A61K 9/48; A61K 35/17; A61K 45/06; A61K 2300/00; A61K 31/454; A61K 2039/505; C07K 16/2878; C07K 16/2887; C07K 16/2893; A61P 35/02

See application file for complete search history.

(56) References Cited

U.S. PATENT DOCUMENTS

| | | |
|---|---|---|
| 8,673,925 B1 | 3/2014 | Goldstein |
| 8,940,744 B2 | 1/2015 | Owens et al. |
| 9,532,990 B2 | 1/2017 | He |
| 9,717,745 B2 * | 8/2017 | He ...................... A61K 31/436 |
| 9,861,636 B2 | 1/2018 | He |
| 10,004,745 B2 | 6/2018 | Buggy et al. |
| 10,098,900 B2 | 10/2018 | He |
| 10,300,066 B2 | 5/2019 | He |
| 10,537,587 B2 | 1/2020 | He |
| 10,596,183 B2 | 3/2020 | He |
| 2004/0127470 A1 | 7/2004 | Masferrer |
| 2012/0108612 A1 | 5/2012 | Honigberg et al. |
| 2016/0200730 A1 | 7/2016 | He |
| 2017/0027941 A1 | 2/2017 | James et al. |
| 2018/0207161 A1 | 7/2018 | He |

FOREIGN PATENT DOCUMENTS

| | | | |
|---|---|---|---|
| CA | 2947338 | 11/2015 | |
| CA | 2980016 A1 * | 9/2016 | ........... A61K 31/436 |
| CN | 102115476 A | 7/2011 | |
| WO | WO 2005/073189 A1 | 8/2005 | |
| WO | WO 2008/058944 | 5/2008 | |
| WO | WO 2008/121742 | 10/2008 | |
| WO | WO 2010/009342 | 1/2010 | |
| WO | WO 2011/046964 | 4/2011 | |
| WO | WO 2012/158764 | 11/2012 | |
| WO | WO 2012/158795 A1 | 11/2012 | |
| WO | WO 2013/010136 | 1/2013 | |
| WO | WO 2013/191965 | 12/2013 | |
| WO | WO 2014/022390 | 2/2014 | |
| WO | WO 2014/022569 | 2/2014 | |
| WO | WO 2014/039899 A1 | 3/2014 | |
| WO | WO 2014/143807 | 9/2014 | |
| WO | WO 2014/166820 | 10/2014 | |

(Continued)

OTHER PUBLICATIONS

Aalipour et al., "Bruton tyrosine kinase inhibitors: a promising novel targeted treatment for B cell lymphomas," Br J Haematol 163(4):436-43 (2013).
Akinleye et al., "Ibrutinib and novel BTK inhibitors in clinical development," Journal of Hematology & Oncology 6:59 (2013).
Berg, "Etiology and pathophysiology of diaper dermatitis," Adv Dermatol. 3:75-98 (1988).
Blum, "B-cell receptor pathway modulators in NHL," Hematology Am Soc Hematol Educ Program 2015:82-91 (2015).
Byrd et al., "Acalabrutinib (ACP-196) in Relapsed Chronic Lymphocytic Leukemia," NEJM 374(4):323-332 (2016).
Cheson et al., "Monoclonal antibody therapy for B-cell non-Hodgkin's lymphoma," NEJM 359(6):613-626 (2008).
Cheson et al., "Revised response criteria for malignant lymphoma," J Clin Oncol 25:579-86 (2007).

(Continued)

*Primary Examiner* — Kortney L. Klinkel
*Assistant Examiner* — Jason Deck
(74) *Attorney, Agent, or Firm* — Steptoe & Johnson LLP; Z. Ying Li; Debashree Chatterjee

(57) ABSTRACT

The present disclosure provides methods of treating lymphoid malignancies such as B cell malignancies using a BTK inhibitor in the described therapeutic regimens.

23 Claims, No Drawings

(56) References Cited

FOREIGN PATENT DOCUMENTS

| WO | WO 2014/168975 | | 10/2014 |
|---|---|---|---|
| WO | WO 2014/172429 | A1 | 10/2014 |
| WO | WO 2014/187319 | A1 | 11/2014 |
| WO | WO 2015/165279 | | 11/2015 |

OTHER PUBLICATIONS

ClinicalTrials.gov "NCT02077166 on Dec. 9, 2015" (2015).

Davis et al., "Chronic active B-cell-receptor signalling in diffuse large B-cell lymphoma," Nature 463:88-92 (2010).

Ezell et al., "Synergistic induction of apoptosis by combination of BTK and dual mTORC½ inhibitors in diffuse large B cell lymphoma," Oncotarget 5(13):4990-5001 (2014).

Fabbro et al., "Panniculitis in Patients Undergoing Treatment with the Bruton Tyrosine Kinase Inhibitor Ibrutinib for Lymphoid Leukemias," JAMA Oncol 1(5):684-686 (2015).

Furman et al., "Ibrutinib Resistance in Chronic Lymphocytic Leukemia," N Engl J Med. 370(24): 2352-2354 (2014).

Griner et al., "High-throughput combinatorial screening identifies drugs that cooperate with ibrutinib to kill activated B-cell-like diffuse large B-cell lymphoma cells," Proc Natl Acad Sci USA 111(6):2349-54 (2014).

Herman et al., "Bruton tyrosine kinase represents a promising therapeutic target for treatment of chronic lymphocytic leukemia and is effectively targeted by PCI-32765," Blood 117(23):6287-6296 (2011).

Hernandez-Ilizaliturri, "Immunomodulatory Drug CC-5013 or CC-4047 and Rituximab Enhance Antitumor Activity in a Severe Combined Immunodeficient Mouse Lymphoma Model," Clinical Cancer Research 11(16):5984-5992 (2005).

Jin et al., "Low dose of lenalidmide and PI3K/mTOR inhibitor trigger synergistic cytoxicity in activated B cell-like subtype of diffuse large B cell lymphoma," J Exp Clin Cancer Res 35:52 (2016).

Kenkre et al., "The future of B-cell lymphoma therapy: the B-cell receptor and its downstream pathways," Curr Hematol Malig Rep 7:216-20 (2012).

Kil et al., "Bruton's tyrosine kinase mediated signaling enhances leukemogenesis in a mouse model for chronic lymphocytic leukemia," Am J Blood Res 3(1):71-83 (2013).

Knutson et al., "Selective inhibition of EZH2 by EPZ-6438 leads to potent antitumor activity in EZH2-mutant non-Hodgkin lymphoma," Mol. Can. Ther 13(4):842-54 (2014).

Kurosaki, "Molecular mechanisms in B cell antigen receptor signaling," Curr OP Imm 9(3):309-18(1997).

Lee et al., "MCL-1-independent mechanisms of synergy between dual PI3K/mTOR and BCL-2 inhibition in diffuse large B cell lymphoma", Oncotarget 6(34) (2015).

Levade et al., "Ibrutinib treatment affects collagen and von Willebrand factor-dependent platelet functions," Blood 124(26):3991-3995 (2014).

Levy et al., "Dications of fluorenylidenes. The effect of substituent electronegativity and position on the antiaromaticity of substituted tetrabenzo[5.5]fulvalene dications," J Org Chem 68(10):3990-3998 (2003).

Li et al., "IMiD immunomodulatory compounds block C/EBP translation through eIF4E down-regulation resulting in inhibition of MM," Blood 117(19):5157-65 (2011).

Marostica et al., "Population pharmacokinetic model of ibrutinib, a Bruton tyrosine kinase inhibitor, in patients with B cell malignancies," Cancer Chemother Pharmacol 75:111-121 (2015).

Novero et al., "Ibrutinib for B cell malignancies," Exp Hematol Oncol 3(1):4 (2014).

Padrnos et al., "A Novel Combination of the mTORCI Inhibitor Everolimus and the Immunomodulatory Drug Lenalidomide Produces Durable Responses in Patients with Heavily Pretreated Relapsed Lymphoma," Clin Lymphoma Myeloma Leuk. 18(10):664-672 (2018).

Raje et al., "Combination of the mTOR inhibitor rapamycin and CC-5013 has synergistic activity in multiple myeloma," Blood 104(13):4188-93 (2004).

Reeder et al., "Novel therapeutic agents for B-cell lymphoma: developing rational combinations," Blood 117(5):1453-62 (2011).

Roschewski et al., "Diffuse large B-cell lymphoma-treatment approaches in the molecular era," Nat Rev Clin Oncol 11(1):12-23 (2014).

Shi et al., "Purine derivatives as potent Bruton's tyrosine kinase (BTK) inhibitors for autoimmune diseases," Bioorg Med Chem Lett 24(9):2206-2211 (2014).

Souers et al., "ABT-199, a potent and selective BCL-2 inhibitor, achieves antitumor activity while sparing platelets," Nat Med 19(2):202-8 (2013).

Swerdlow et al., "The 2016 revision of the World Health Organization classification of lymphoid neoplasms," Blood 127(20):2375-2390 (2016).

Tabe et al., "Selective inhibitor of nuclear export selinexor (KPT-330) and BCL2 inhibitor ABT-199 enhance the anti-lymphoma effect of BTK inhibitor ibrutinib in mantle cell lymphoma," Blood 124:2254 (2014).

Vargas et al, "Inhibitors of BTK and ITK: state of the new drugs for cancer, autoimmunity and inflammatory diseases," Scand J Immunol 78(2):130-139 (2013).

Wang et al., "CD19: a biomarker for B cell development, lymphoma diagnosis and therapy," Exp Hematol Oncol 1(1):36 (2012).

Wang et al., "Targeting BTK with ibrutinib in relapsed or refractory mantle-cell lymphoma," NEJM 369(6):507-516 (2013).

Wanner et al., "Mammalian target of rapamycin inhibition induces cell cycle arrest in diffuse large B cell lymphoma (DLBCL) cells and sensitises DLBCL cells to rituximab," Br J Haematol 134(5):475-84 (2006).

Wiestner, J., "Targeting B-Cell receptor signaling for anticancer therapy: the Bruton's tyrosine kinase inhibitor ibrutinib induces impressive responses in B-cell malignancies," Clin Oncol 31:128-30 (2013).

Yang et al., "Exploiting Synthetic Lethality for the Therapy of ABC Diffuse Large B Cell Lymphoma," Cancer Cell 21(6):723-737 (2012).

Zhao et al., "Combination of ibrutinib with ABT-199, a BCL-2 pathway inhibitor: effective therapeutic strategy in a novel mantle cell lymphoma cell line model," Blood 122(21): 645 (2013).

Wang et al., "Ibrutinib in Combination with Rituximab in Relapsed or Refractory Mantle Cell Lymphoma: A Single-Centre, Open-Label, Phase 2 Trial," Lancet Oncology 17: 48-56 (2016).

* cited by examiner

METHODS FOR TREATING LYMPHOID MALIGNANCIES

CROSS REFERENCE TO RELATED APPLICATIONS

The present application is a national stage under 35 U.S.C. § 371 of International Patent Application PCT/US2018/057660, filed Oct. 26, 2018, which claims priority from U.S. Provisional Application 62/578,081, filed Oct. 27, 2017. The disclosures of these applications are incorporated by reference herein in their entirety.

BACKGROUND OF THE INVENTION

B-cell lymphoma is the most common type of non-Hodgkin lymphoma (NHL) with a wide range of clinical and histological features (Swerdlow et al., Blood 127(20):2375-2390 (2016); Cheson et al., NEJM 359(6):613-626 (2008)). Although the addition of rituximab to chemotherapy has improved the outcome of patients with B-cell lymphoma, relapse/refractory disease still occurs due to the high heterogeneity of B-cell lymphoma (Cheson, supra). Therefore, relapsed/refractory B-cell lymphoma has become the focus of current laboratory and clinical research, and novel agents are urgently needed.

Previous studies have reported that the survival and proliferation of malignant B cells depend on the constitutive activation of the B-cell receptor (BCR) signaling pathway (Wiestner, J Clin Oncol 31:128-30 (2013); Davis et al., Nature 463:88-92 (2010); Kenkre et al., Curr Hematol Malig Rep 7:216-20 (2012)). As a downstream molecule in this pathway, Bruton's tyrosine kinase (BTK) plays a critical role in BCR signaling and B-cell development and function (Herman et al., Blood 117(23):6287-6296 (2011); Wang et al., Exp Hematol Oncol 1(1):36 (2012)). Therefore, targeted therapy against BTK has been in active clinical development (Novero et al., Exp Hematol Oncol 3(1):4 (2014); Aalipour et al., Br J Haematol. 163(4):436-443 (2013); Byrd et al., NEJM 374(4):323-332 (2016)).

Ibrutinib, as a first-generation BTK inhibitor, has been approved by the U.S. Food and Drug Administration (FDA) as breakthrough therapy for the treatment of various types of B-cell lymphoma. Several clinical studies have demonstrated the efficacy of ibrutinib as monotherapy in relapsed/refractory B-cell lymphomas (Wang et al., NEJM 369(6):507-516 (2013); Blum, Hematology Am Soc Hematol Educ Program 2015:82-91 (2015)). However, adverse events, such as bleeding, atrial fibrillation, and rash, have been reported and are believed to be due to the off-target effects of ibrutinib (Fabbro et al., JAMA Oncol 1(5):684-686 (2015); Levade et al., Blood 124(26):3991-3995 (2014); Furman et al., NEJM 370(24):2352-2354 (2014)). Meanwhile, the inter-patient pharmacokinetic (PK) exposures vary significantly from patient to patient. Therefore, better BTK-targeting therapies are urgently needed.

SUMMARY OF THE INVENTION

The present disclosure relates to a method of treating a lymphoid malignancy in a human patient in need thereof. The method comprises administering to the patient a BTK inhibitor, such as 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one (Compound A), or an enantiomer, a diastereomer, a pharmaceutically acceptable salt, or a prodrug thereof, in one or more treatment cycles, wherein Compound A is administered to the patient at a daily dose of 50-400 mg for 14-28 treatment days in each treatment cycle. In some embodiments, the treatment cycle is repeated one or more times. In some embodiments, each treatment cycle is 21-35 days.

In some embodiments, the method comprises administering to the patient Compound A (i) 14 treatment days every 21 days, (ii) 21 treatment days every 28 days, (iii) 28 treatment days every 28 days, or (iv) 28 treatment days every 35 days. The treatment days may be consecutive or non-consecutive.

In some embodiments, the daily dose of Compound A is 50, 100, 150, 200, 300, or 400 mg.

In some embodiments, the lymphoid malignancy is a B-cell malignancy, such as relapsed or refractory B-cell malignancy, B-cell lymphoma, non-Hodgkin B-cell lymphoma (e.g., chronic lymphocytic leukemia (CLL), small lymphocytic lymphoma (SLL), follicular lymphoma (FL), diffuse large B-cell lymphoma (DLBCL), Waldenström's Macroglobulinemia (WM), marginal zone lymphoma (MZL), and mantle cell lymphoma (MCL)). In particular embodiments, the non-Hodgkin B-cell lymphoma is DLBCL.

In some embodiments, Compound A is administered in combination with a therapeutic monoclonal antibody or a derivative thereof, or with chimeric antigen receptor (CAR) T-cell therapy. In some embodiments, the therapeutic monoclonal antibody or the CAR T-cell therapy targets a cell surface receptor on B cells, and wherein optionally the cell surface receptor is CD20, CD30, or CD52. The therapeutic monoclonal antibody may be selected from the group consisting of rituximab, obinutuzumab, ofatumumab, ibritumomab tiuxetan, alemtuzumab, and brentuximab vedotin.

Some of the treatment methods further comprise administering a therapeutically effective amount of a mammalian target of rapamycin (mTOR) inhibitor to the patient in said one or more treatment cycles.

In some embodiments, the mTOR inhibitor is selected from the group consisting of everolimus, rapamycin, [7-(6-Amino-3-pyridinyl)-2,3-dihydro-1,4-benzoxazepin-4(5H)-yl][3-fluoro-2-methyl-4-(methylsulfonyl)phenyl]-methanone (XL388), N-ethyl-N'-[4-[5,6,7,8-tetrahydro-4-[(3 S)-3-methyl-4-morpholinyl]-7-(3-oxetanyl)pyrido[3,4-d]pyrimidin-2-yl]phenyl]-Urea (GDC-0349), 3-(2,4-bis((S)-3-methylmorpholino)pyrido[2,3-d]pyrimidin-7-yl)-N-methylbenzamide (AZD2014), (5-(2,4-bis((S)-3-methylmorpholino)pyrido[2,3-d]pyrimidin-7-yl)-2-methoxyphenyl)methanol (AZD8055), GSK105965, 3-(2-aminobenzo[d]oxazol-5-yl)-1-isopropyl-1H-pyrazolo[3,4-d]pyrimidin-4-amine (TAK-228 or MLN0128), temsirolimus, ridaforolimus, PI-103, NVP-BEZ235, WJDO08, XL765, SF-1126, Torin1, PP242, PP30, Ku-0063794, WYE-354, WYE-687, WAY-600, INK128, OSI 027, gedatolisib (PF-05212384), CC-223, LY3023414, PQR309, LXI-15029, SAR245409, and pharmaceutically acceptable salts and prodrugs thereof. In some embodiments, the treatment methods herein comprises administering everolimus to the patient at a daily dose of 0.5-25 mg on said treatment days, e.g., 0.5, 1, 1.25, 1.5, 2.5, 3.75, or 5 mg daily.

Some of the above combination treatment methods further comprise administering a therapeutically effective amount of an immunomodulatory drug (IMiD) to the patient in said one or more treatment cycles (e.g., a triplet combination of BTK inhibition, mTOR inhibitor, and IMiD). In some embodiments, the IMiD is thalidomide, lenalidomide, pomalidomide, CC-112, CC-220, or a pharmaceutically acceptable salt or a prodrug thereof. In some embodiments, the treatment methods comprise administering pomalidomide to the patient at a daily dose of 0.2-4, 0.5-3, 1-3, 1-2, or 2-3 mg on treatment days, e.g., 0.33, 0.5, 0.67, 1, 2, 3, or 4 mg daily.

In some embodiments, the treatment method comprises administering to the patient one or more (e.g., two or three) tablets or capsules each comprising (a) 100 mg of Compound A and (b) 1.25 mg of everolimus p.o for (i) 14 treatment days in a 21-day treatment cycle, (ii) 21 treatment days in a 28-day treatment cycle, (iii) 28 treatment days in a 28-day treatment cycle, or (iv) 28 treatment days in one or more 35-day treatment cycles.

In some embodiments, the treatment method comprises administering to the patient one or more (e.g., two or three) tablets or capsules each comprising (a) 100 mg of Compound A, (b) 1.25 mg of everolimus, and (c) 0.33, 0.5, or 0.67 mg pomalidomide p.o for (i) 14 treatment days in a 21-day treatment cycle, (ii) 21 treatment days in a 28-day treatment cycle, (iii) 28 treatment days in a 28-day treatment cycle, or (iv) 28 treatment days in one or more 35-day treatment cycles.

In the methods herein, the patient may be given the therapeutic agents p.o. (i.e., orally).

Also included in the present disclosure is a pharmaceutical composition comprising 100 mg of Compound A, 1.25 mg of everolimus, and a pharmaceutically acceptable excipient. In some embodiments, the pharmaceutical composition further comprises 0.33, 0.5, or 0.67 mg pomalidomide. In some embodiments, the pharmaceutical composition is a tablet or a capsule.

Also included in the present disclosure are the use of Compound A in the manufacture of a medicament for the treatment of a lymphoid malignancy in a method described herein, Compound A for use in treating a lymphoid malignancy in a method described herein, a pharmaceutical composition such as the one described above for use in a method described herein, and Compound A-containing kits and articles of manufacture for use in a method described herein.

DETAILED DESCRIPTION OF THE INVENTION

The present disclosure provides new treatment methods for lymphoid malignancies, such as B-cell malignancies, using a BTK inhibitor such as Compound A. A variety of lymphoid malignancies may be treated by the disclosed methods, including, but not limited to, small lymphocytic lymphoma (SLL), prolymphocytic leukemia (PLL), acute lymphocytic leukemia (ALL), chronic lymphocytic leukemia (CLL), Richter's syndrome, diffuse large B-cell lymphoma (DLBCL), Waldenström Macroglobulinemia (WM), follicular lymphoma (FL), multiple myeloma, mantle cell lymphoma (MCL), marginal zone lymphoma (MZL), Hodgkin lymphoma, and non-Hodgkin lymphoma. In some embodiments, the B-cell malignancy treated may be relapsed or refractory B-cell malignancy. In some embodiments, the B-cell malignancy treated is DLBCL.

Compound A is a selective, irreversible and potent BTK inhibitor with an $IC_{50}$ value of 0.7 nM. See, e.g., U.S. Pat. No. 9,717,745 (Compound A is compound 3 in the patent); and U.S. Pat. No. 9,532,990 (Compound A is compound 45 in the patent). Both patents are incorporated by reference herein in their entirety. Compound A has been shown to have no off-target inhibitory activities in off-target screenings against 104 proteins (e.g., transporters, cell receptors, ion channels, and enzymes). Against a 46 kinase panel, Compound A has been shown to exhibit partial inhibition of EGFR, FGFR1, FGFR2 and JAK3 kinases only, with the $IC_{50}$ against EGFR kinase being 110 nM. Improved toxicokinetics properties of Compound A in rats and beagle dogs further suggest that Compound A may have better pharmacokinetic properties in human patients.

Synthetic lethality is characterized by the chemical inhibition of multiple aberrant genes to differentially kill malignant cells while sparing normal cells. The present disclosure describes that synthetic lethality of tumor cells can be achieved through BTK inhibitors such as Compound A administered in accordance with the dosing regimens described herein, including the dosing regimens of the best-in-class combinations of targeted agents with synergistic action at low doses.

BTK Inhibitor Therapy

The present disclosure provides data obtained in first-in-human monotherapy trials in China and in the United States. The trials were conducted with escalating doses of Compound A from 50 mg, 100 mg, 200 mg, to 400 mg daily. The primary endpoint of the trials was safety, while the secondary endpoints of the trials were anti-tumor activity and pharmacokinetic parameters. Patients enrolled in the trials met the following criteria: relapsed/refractory CLL and B-cell lymphoma with no available effective therapies, ≥18 years of age, and an Eastern Cooperative Oncology Group (ECOG) score≤1. Compound A was administered for 28 consecutive days in a 35-day cycle (i.e., 28 days of treatment, followed by a week of no treatment) in the China trial, and for 21 consecutive days of a 28-day cycle (i.e., 21 days of treatment, followed by a week of no treatment) in the U.S. trial. The treatment cycle was repeated until disease progression or unacceptable toxicity was observed. The 3+3 dose-escalation method was used. Data from the trials show that Compound A is safe and well tolerated in patients with relapsed/refractory B-cell lymphomas. Efficacy of the Compound has also been observed in patients with Waldenström Macroglobulinemia, marginal zone lymphoma, and small lymphocytic lymphoma/chronic lymphocytic leukemia who took Compound A orally at 50-400 mg once daily. See also Example 1 below.

The BTK inhibitor useful in the present treatment methods may be Compound 1, Compound 2, Compound 3 (Compound A), Compound 4, Compound 5, Compound 6, Compound 7, or Compound 8 as shown in Table 1, or an enantiomer, a diastereomer, a pharmaceutically acceptable salt, or a prodrug thereof. In some embodiments, the BTK inhibitor is Compound A. The synthesis and characterization of the above BTK inhibitory compounds are described in U.S. Pat. No. 9,532,990, which is incorporated herein by reference in its entirety.

TABLE 1
Representative BTK Inhibitor Compounds
| Compound No. | Structure | Name |
|---|---|---|
| 1 | 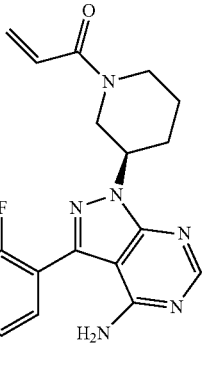 | 1-((R)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one |
| 2 | 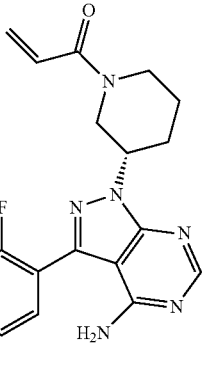 | 1-((S)-3-(4-amino-3-(2-fluoro-4-(2,3,5,6-tetrafluorophenoxy)phenyl)-1H-pyrazolo[3,4-d]pyrimidin-1-yl)piperidin-1-yl)prop-2-en-1-one |
| 3 | 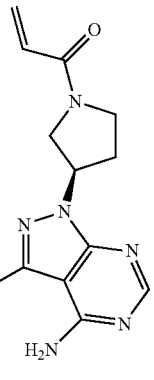 | 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one |

TABLE 1-continued

Representative BTK Inhibitor Compounds

| Compound No. | Structure | Name |
| --- | --- | --- |
| 4 | 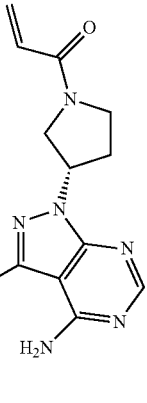 | 1-((S)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one |
| 5 | 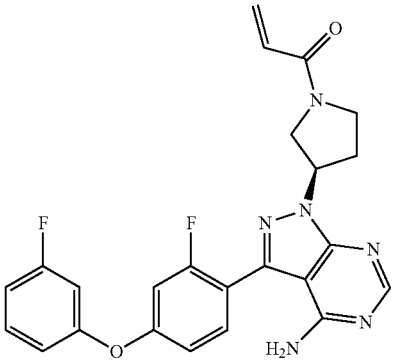 [SMILES: C=CC(=O)N1CC[C@@H](n2nc(-c3ccc(Oc4cccc(F)c4)cc3F)c3c(N)ncnc32)C1] | 1-((R)-3-(4-amino-3-(2-fluoro-4-(3-fluorophenoxy)phenyl)-1H-pyrazolo[3,4-d]pyrimidin-1-yl)pyrrolidin-1-yl)prop-2-en-1-one |
| 6 | 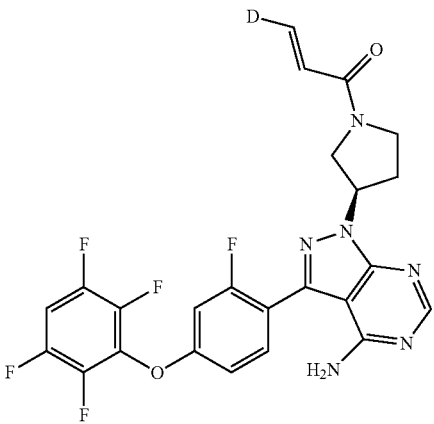 [SMILES: [2H]/C=C/C(=O)N1CC[C@@H](n2nc(-c3ccc(Oc4c(F)c(F)cc(F)c4F)cc3F)c3c(N)ncnc32)C1] | (E)-1-((R)-3-(4-amino-3-(2-fluoro-4-(3-fluorophenoxy)phenyl)-1H-pyrazolo[3,4-d]pyrimidin-1-yl)pyrrolidin-1-yl)-3-deuterium-prop-2-en-1-one |

TABLE 1-continued

Representative BTK Inhibitor Compounds

| Compound No. | Structure | Name |
|---|---|---|
| 7 | 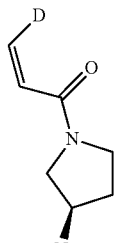 | (Z)-1-((R)-3-(4-amino-3-(2-fluoro-4-(3-fluorophenoxy)phenyl)-1H-pyrazolo[3,4-d]pyrimidin-1-yl)pyrrolidin-1-yl)-3-deuterium-prop-2-en-1-one |
| 8 | 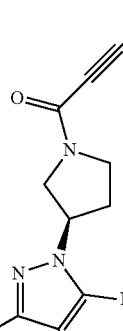 | 1-((R)-3-(4-amino-3-(2-fluoro-4-(3-fluorophenoxy)phenyl)-1H-pyrazolo[3,4-d]pyrimidin-1-yl)pyrrolidin-1-yl)but-2-yn-1-one |

Note:
If there are differences between the structure and the name, the structure will prevail.

In other embodiments, a BTK inhibitor selected from the following list may be used: ibrutinib, ACP-196 (acalabrutinib), BGB-3111, spebrutinib, ONO-4059, HM71224, RN486, 4-(4-((4-((3-acrylamidophenyl)amino)-5-fluoropyrimidin-2-yl)amino)phenoxy)-N-methylpicolinamide (CNX-774), N-[3-[4-[4,5-dihydro-4-methyl-6-[[4-(4-(4-morpholinylcarbonyl)phenyl]amino]-5-oxopyrazinyl]-2-methylphenyl]-4-(1,1-dimethylethyl)-benzamide (CGI-1746), AVL-292 (CC-292), PRN1008, M7583, M2951, BIIB068, CT-1530, AC0058TA, ARQ 531, GS-4059, REDX08608, RXC005, BMS-986142, TP-0158, SNS-062, and BI-BTK-1, or a pharmaceutically acceptable salt or prodrug thereof.

As used herein, a "prodrug" is a biologically inactive compound that can be metabolized in the body to produce a drug. For example, a prodrug of a BTK inhibitor can be a prodrug at the amino group, for example, an amide, carbamate, or a polyethylene glycol.

As used herein, the term "pharmaceutically acceptable salts" refers to salts formed with acid or base, including, but not limited to, (a) acid addition salts: inorganic acid (e.g., hydrochloric acid, hydrobromic acid, sulfuric acid, phosphoric acid, nitric acid and other organic acids), and organic acid (e.g., acetic acid, oxalic acid, tartaric acid, succinic acid, malic acid, and ascorbic acid); and (b) base addition salts, the formation of metal cations, such as zinc, calcium, sodium, and potassium.

In a treatment method of the present disclosure, BTK inhibitors such as those described herein may be administered to the patient at a dose of 10-500, 25-450, 50-400, 50-200, 100-300, 100-400, or 200-400 mg daily, e.g., 10, 25, 50, 100, 200, 300, or 400 mg daily. When used in combination therapies such as those described herein, the dosage of the BTK inhibitory compound may be lower than when the compound is used alone in a monotherapy.

In some embodiments, the BTK inhibitor is administered for 10-40, 10-35, 14-21, 14-28, or 20-30 days (i.e., treatment days, which may be consecutive or non-consecutive) in a 15-50, 15-45, 21-28, 21-35, or 25-40 day treatment cycle, where the treatment cycle may have one or more non-treatment days and may be repeated once or more than once, until the patient reaches a desired therapeutic endpoint or until disease progression or unacceptable toxicity occurs in the patient. For example, the BTK inhibitor may be administered for (i) 14 consecutive treatment days in a 21-day cycle, (ii) 21 consecutive treatment days in a 28-day cycle, or (iii) 28 consecutive treatment days in a 35-day cycle, where the cycle is repeated one or more times, until the patient reaches a desired therapeutic endpoint or until disease progression or unacceptable toxicity occurs in the patient.

In some embodiments, the BTK inhibitor may be administered daily in a continuous fashion until the patient reaches a desired therapeutic endpoint or until disease progression or unacceptable toxicity occurs in the patient. For example, the patient may be treated with the BTK inhibitor 28 consecutive days in repeated 28-day cycles, where the patient's conditions may be assessed at least once in every treatment cycle.

Combination Therapy

Another aspect of the present disclosure relates to a method of treating a lymphoid malignancy such as a B-cell malignancy in a human patient using a combination therapy including a BTK inhibitor and a mammalian target of rapamycin (mTOR) inhibitor. In some embodiments, the combination therapy also includes an IMiD. The present disclosure provides data on the oral doublet therapy with Compound A and everolimus, and the oral triplet therapy with Compound A, everolimus, and pomalidomide from the U.S. clinical trial. See Examples 2-4 below.

In some embodiments, a therapeutically effective amount of the BTK inhibitor is administered in combination with a therapeutically effective amount of mTOR inhibitor. The mTOR protein is a protein kinase that serves as a key regulator of cell growth, proliferation, metabolism and apoptosis. Inhibitors of mTOR useful in the combination therapy of this invention include but are not limited to everolimus,
rapamycin (sirolimus),
[7-(6-Amino-3-pyridinyl)-2,3-dihydro-1,4-benzoxazepin-4(5H)-yl][3-fluoro-2-methyl-4-(methylsulfonyl)phenyl]-methanone (XL388),
N-ethyl-N'-[4-[5,6,7,8-tetrahydro-4-[(3S)-3-methyl-4-morpholinyl]-7-(3-oxetanyl)pyrido[3,4-d]pyrimidin-2-yl]phenyl]-Urea (GDC-0349 (Genentech)),
3-(2,4-bis((S)-3-methylmorpholino)pyrido[2,3-d]pyrimidin-7-yl)-N-methylbenzamide (AZD2014 (AstraZeneca)),
(5-(2,4-bis((S)-3-methylmorpholino)pyrido[2,3-d]pyrimidin-7-yl)-2-methoxyphenyl)methanol (AZD8055),
GSK105965,
3-(2-aminobenzo[d]oxazol-5-yl)-1-isopropyl-1H-pyrazolo[3,4-d]pyrimidin-4-amine (TAK-228 or MLN0128 (Takeda)),
temsirolimus,
ridaforolimus,
PI-103,
NVP-BEZ23 5,
WJD008,
XL765,
SF-1126,
Torin1,
PP242,
PP30,
Ku-0063794,
WYE-354,
WYE-687,
WAY-600,
INK128,
OSI-027,
gedatolisib or PF-05212384 (Pfizer),
CC-223 (Celgene),
LY3023414 (Lilly),
PQR309 (PIQUR Therapeutics),
LXI-15029 (Luoxin Pharma),
SAR245409 (Sanofi), and pharmaceutically acceptable salts thereof.

In some embodiments, everolimus is used in the combination therapy as an mTOR inhibitor. It may be administered at a dose of 0.1-30, 0.5-25, 0.75-20, 1-17.5, 1.5-15, 2-10, 2-7.5, 0.5-5, or 2.5-5 mg daily, e.g., 1.25, 2, 2.5, 3, 3.75, 4, or 5 mg daily. Everolimus has been approved by the United States Food and Drug Administration for the treatment of breast cancer, pancreatic cancer, renal cell carcinoma, renal angiomyolipoma, and tuberous sclerosis. In addition, everolimus has been used to treat organ transplant rejection at low doses, as organ transplant also activates mTOR. The inventor contemplates that the combination therapy of the present disclosure also can be used in these contexts.

In some embodiments, the BTK inhibitor is administered in combination with the therapeutically effective amount of the mTOR inhibitor for 10-40, 10-35, 14-21, 14-28, or 20-30 treatment days (e.g., consecutive days) in a 15-50, 15-45, 21-28, 21-35, or 25-40 day treatment cycle, where the treatment cycle may have one or more non-treatment days and may be repeated once or more than once, until the patient reaches a desired therapeutic endpoint or until disease progression or unacceptable toxicity occurs in the patient. For example, the BTK inhibitor and the mTOR inhibitor may be administered on the same day (e.g., in separate compositions or a single composition) to the patient for (i) 14 consecutive days in a 21-day cycle, (ii) 21 consecutive days in a 28-day cycle, or (iii) 28 consecutive days in a 35-day cycle, where the cycle may be repeated one or more times, until the patient reaches a desired therapeutic endpoint or until disease progression or unacceptable toxicity occurs in the patient.

In some embodiments, the BTK inhibitor and the mTOR inhibitor may be administered daily in a continuous fashion until the patient reaches a desired therapeutic endpoint or until disease progression or unacceptable toxicity occurs in the patient. For example, the patient may be treated with the two inhibitors on the same day (e.g., in separate compositions or a single composition) for 28 consecutive days in repeated 28-day cycles, where the patient's conditions may be assessed at least once in every treatment cycle.

In further embodiments, the patient is treated with a therapeutically effective amount of the BTK inhibitor, a therapeutically effective amount of the mTOR inhibitor, and a therapeutically effective amount of an immunomodulatory drug (IMiD) in a combination therapy, where the three compounds may be administered in separate compositions or in a single composition. Immunomodulatory drugs (IMiDs) are a class of drugs that include thalidomide and its structural and functional analogues. IMiDs possess anti-angiogenic, anti-proliferative and pro-apoptotic properties for cancer cells. IMiDs stimulate T lymphocytes to induce proliferation, cytokine production, and cytotoxicity, thus increasing T cells' anti-cancer activities. IMiDs are useful in treating a variety of inflammatory and autoimmune diseases. IMiDs also are useful in treating neoplastic diseases such as hematologic neoplasms, e.g., multiple myeloma and myelodysplastic syndromes, as well as certain solid tumors. IMiDs such as lenalidomide, pomalidomide, CC-112 (Celgene), and CC-220 (Celgene) have improved potency and reduced side effects compared to thalidomide. In some embodiments, the IMiD is thalidomide, lenalidomide, pomalidomide, CC-112, CC-220, or a pharmaceutically acceptable salt or prodrug thereof. In some embodiments, the IMiD is pomalidomide or a pharmaceutically acceptable salt thereof in the amount of 0.2-4, 0.5-3, 1-3, 1-2, or 2-3 mg daily, e.g., 0.33, 0.5, 0.67, 1, 2, 3, or 4 mg daily.

In some embodiments, the combination of the BTK inhibitor, the mTOR inhibitor, and the IMiD is administered to the patient for 10-40, 10-35, 14-21, 14-28, or 20-30 treatment days (e.g., consecutive days) in a 15-50, 15-45, 21-28, 21-35, or 25-40 day treatment cycle, where the treatment cycle may have one or more non-treatment days and may be repeated once or more than once, until the patient reaches a desired therapeutic endpoint or until disease progression or unacceptable toxicity occurs in the patient. For example, the three compounds may be administered on the same day (e.g., in separate compositions or a single composition) to the patient for (i) 14 consecutive days in a 21-day cycle or (ii) 21 consecutive days in a 28-day cycle, where the cycle may be repeated one or more times, until the patient reaches a desired therapeutic endpoint or until disease progression or unacceptable toxicity occurs in the patient.

In some embodiments, the BTK inhibitor, the mTOR inhibitor, and the IMiD may be administered daily in a continuous fashion until the patient reaches a desired therapeutic endpoint or until disease progression or unacceptable toxicity occurs in the patient. For example, the patient may be treated with the three inhibitors on the same day (e.g., in separate compositions or a single composition) for 28 consecutive days in repeated 28-day cycles, where the patient's conditions may be assessed at least once in every treatment cycle.

In other embodiments, the BTK inhibitor alone, the combination of the BTK inhibitor and the mTOR inhibitor, or the combination of the BTK inhibitor, the mTOR inhibitor, and the IMiD is administered in further combination with a therapeutic monoclonal antibody or its derivative to treat a lymphoid malignancy such as a B-cell malignancy. Non-limiting examples of the therapeutic monoclonal antibody or its derivative include rituximab, obinutuzumab, ofatumumab, ibritumomab tiuxetan, alemtuzumab, and brentuximab vedotin. Rituximab, obinutuzumab, ofatumumab, and ibritumomab tiuxetan are directed at the B-cell surface antigen CD20. Alemtuzumab is a monoclonal antibody targeting CD52. Brentuximab vedotin is an anti-CD30 antibody attached to a chemotherapy drug.

In some embodiments, the present disclosure relates to a method of treating a lymphoid malignancy such as a B-cell malignancy in a human patient in need thereof comprising administering to the patient (a) Compound A at a dose of 10-500, 25-450, 50-400, 50-200, 100-400, 100-300, or 200-400 mg daily; and (b) everolimus at a dose of 0.5-25, 0.75-20, 1-17.5, 1.5-15, 2-10, 2-7.5, 0.5-5, or 2.5-5 mg daily, e.g., 0.5, 1, 1.25, 1.5, 2, 2.5, 3, 3.75, 4, or 5 mg daily. The B-cell malignancy is small lymphocytic lymphoma (SLL), mantle cell lymphoma (MCL), follicular lymphoma (FL), diffuse large B-cell lymphoma (DLBCL), Waldenström's Macroglobulinemia (WM), marginal zone lymphoma (MZL), or chronic lymphocytic leukemia (CLL). In particular embodiments, the B-cell malignancy is DLBCL. In one embodiment, the dose of Compound A is 100-300 mg daily, and the dose of everolimus is 1.25, 2.5, 3.75, or 5 mg daily. In another embodiment, the dose of Compound A is 200-400 mg daily, and the dose of everolimus is 0.5, 1, 1.25, 1.5, 2.5, 3.75, or 5 mg daily. Generally, when the dose of Compound A is increased, the dose of everolimus may be advantageously reduced without reducing the therapeutic efficacy. In some embodiments, the administering is performed daily in a continuous fashion. In some embodiments, the administering is performed for 14 consecutive days in repeated 21-day cycles until a desired clinical endpoint is reached, or until disease progression or unacceptable toxicity occurs. In some embodiments, the administering is performed for 21 consecutive days in repeated 28-day cycles until a desired clinical endpoint is reached, or until disease progression or unacceptable toxicity occurs. In some embodiments, the administering is performed for 28 consecutive days in repeated 28-day cycles until a desired clinical endpoint is reached, or until disease progression or unacceptable toxicity occurs. In some embodiments, the administering is performed for 28 consecutive days in repeated 35-day cycles until a desired clinical endpoint is reached, or until disease progression or unacceptable toxicity occurs.

In some embodiments, the daily doses of Compound A and everolimus in the doublet combination therapy are as indicated in the following table:

TABLE 2

| Everolimuls | Cmpd A | | | | | | | | | |
|---|---|---|---|---|---|---|---|---|---|---|
| | 50-400 mg | 100-400 mg | 100-300 mg | 200-400 mg | 50-200 mg | 50 mg | 100 mg | 200 mg | 300 mg | 400 mg |
| 2-10 mg | X | X | X | X | X | X | X | X | X | X |
| 2-7.5 mg | X | X | X | X | X | X | X | X | X | X |
| 0.5-5 mg | X | X | X | X | X | X | X | X | X | X |
| 2.5-5 mg | X | X | X | X | X | X | X | X | X | X |
| 0.5 mg | X | X | X | X | X | X | X | X | X | X |
| 1 mg | X | X | X | X | X | X | X | X | X | X |
| 1.25 mg | X | X | X | X | X | X | X | X | X | X |
| 1.5 mg | X | X | X | X | X | X | X | X | X | X |
| 2 mg | X | X | X | X | X | X | X | X | X | X |
| 2.5 mg | X | X | X | X | X | X | X | X | X | X |
| 3 mg | X | X | X | X | X | X | X | X | X | X |
| 3.75 mg | X | X | X | X | X | X | X | X | X | X |
| 4 mg | X | X | X | X | X | X | X | X | X | X |
| 5 mg | X | X | X | X | X | X | X | X | X | X |

*Cmpd: Compound. X: combination therapy of everolimus and Compound A at the indicated dosages.

In some embodiments, the present disclosure relates to a method of treating a lymphoid malignancy such as a B-cell malignancy in a human patient in need thereof comprising administering to the patient (a) Compound A at a dose of 10-500, 25-450, 50-400, 50-200, 100-400, 100-300, or 200-400 mg daily; (b) everolimus at a dose of 0.5-25, 0.75-20, 1-17.5, 1.5-15, 2-10, 2-7.5, 0.5-5, or 2.5-5 mg daily, e.g., 0.5, 1, 1.25, 1.5, 2, 2.5, 3, 3.75, 4, or 5 mg daily; and (c) pomalidomide at a dose of 0.2-4, 0.5-3, 1-3, 1-2, or 2-3 mg daily, e.g., 0.33, 0.5, 0.67, 1, 2, 3, or 4 mg daily. The B-cell malignancy may be small lymphocytic lymphoma (SLL), mantle cell lymphoma (MCL), follicular lymphoma (FL), diffuse large B-cell lymphoma (DLBCL), Waldenström's Macroglobulinemia (WM), marginal zone lymphoma (MZL), or chronic lymphocytic leukemia (CLL). In particular embodiments, the B-cell malignancy is DLBCL. Generally, when the dose of Compound A is increased, the dose of everolimus and/or IMiD or vice versa may be advantageously reduced without reducing the therapeutic efficacy. In one embodiment, the dose of Compound A is 100-300 mg daily, and the dose of everolimus is 1.25, 2.5, 3.75 or 5 mg daily. In another embodiment, the dose of Compound A is 200-400 mg daily, and the dose of everolimus is 0.5, 1, 1.25, 1.5, 2.5, 3.75, or 5 mg daily. In some embodiments, the combination of Compound A, everolimus, and pomalidomide is administered to the patient for 10-40, 10-35, 14-21, 14-28, or 20-30 treatment days (e.g., consecutive days) in a 15-50, 15-45, 21-28, 21-35, or 25-40 day treatment cycle, where the treatment cycle may have one or more non-treatment days and may be repeated once or more than once, until the patient reaches a desired therapeutic endpoint or until disease progression or unacceptable toxicity occurs in the patient. In some embodiments, the administering is performed daily in a continuous fashion (e.g., 28-day administration out of a 28-day cycle) until the patient reaches a desired therapeutic endpoint, or until disease progression or unacceptable toxicity occurs in the patient. In some embodiments, the administering is performed for 21 consecutive days in repeated 28-day cycles until the patient reaches a desired therapeutic endpoint or until disease progression or unacceptable toxicity occurs in the patient. In other embodiments, the administering is performed for 14 consecutive days in repeated 21-day cycles until the patient reaches a desired therapeutic endpoint or until disease progression or unacceptable toxicity occurs in the patient.

In some embodiments, the daily dose of pomalidomide is 0.2-4, 0.5-3, 1-3, 1-2, or 2-3 mg, e.g., 0.33, 0.5, 0.67, 1, 2, 3, or 4 mg, and at each said daily dose of pomalidomide, the daily doses of Compound A and everolimus in the triplet combination therapy are as indicated in Table 2 above.

In the present disclosure, when the multiple therapeutic agents (e.g., BTK inhibitor, mTOR inhibitor, the IMiD, and/or the therapeutic monoclonal antibody) are administered to the patient, the agents may be administered sequentially, in any order. Alternatively, the agents in the combination may be administered at the same time, e.g., in separate pharmaceutical compositions concurrently, or as in the same, co-formulated pharmaceutical composition. Still alternatively, some of the agents in the combination may be administered simultaneously while the other agent(s) are administered separately.

In some embodiments, each of the BTK inhibitor, the mTOR inhibitor, and the IMiD is orally (i.e., per os or p.o.) administered to the patient one or more times daily.

Table 3 below shows the structures of some of the compounds useful in the present invention.

TABLE 3

| Entry | Compound Name | Structure |
|---|---|---|
| 1 | ACP-196 (acalabrutinib) | 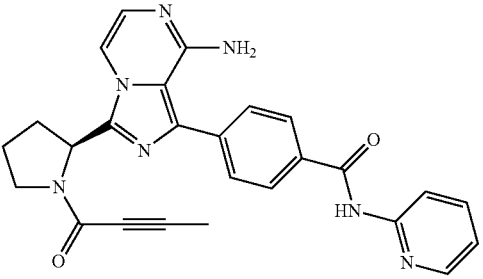 [SMILES: CC#CC(=O)N1CCC[C@H]1c1nc(-c2ccc(C(=O)Nc3ccccn3)cc2)c2c(N)nccn12] |
| 2 | AVL-292 (CC-292) | 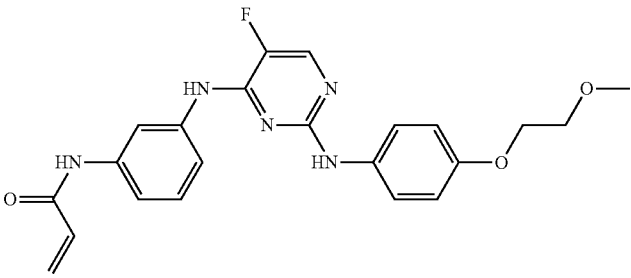 [SMILES: C=CC(=O)Nc1cccc(Nc2nc(Nc3ccc(OCCOC)cc3)ncc2F)c1] |

TABLE 3-continued
| Entry | Compound Name | Structure |
|---|---|---|
| 3 | ONO-4059 | 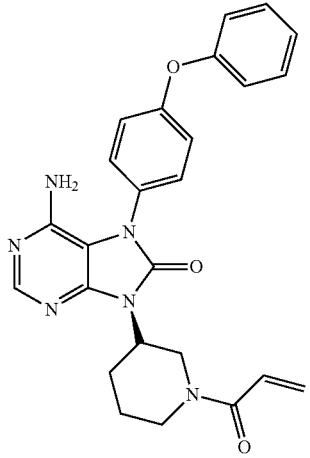 |
| 4 | HM71224 (olmutinib) | 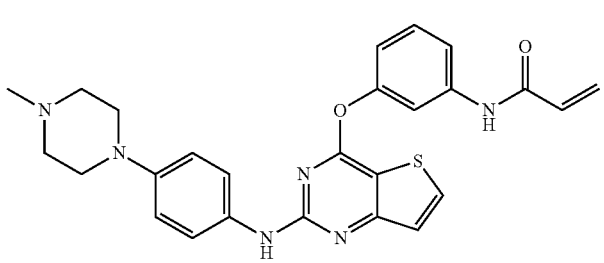 [SMILES: C=CC(=O)Nc1cccc(Oc2nc(Nc3ccc(N4CCN(C)CC4)cc3)nc3ccsc23)c1] |
| 5 | RN486 | 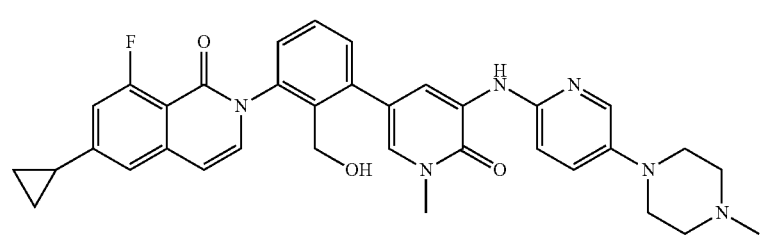 [SMILES: CN1CCN(c2ccc(Nc3cc(-c4cccc(-n5ccc6cc(C7CC7)cc(F)c6c5=O)c4CO)cn(C)c3=O)nc2)CC1] |
| 6 | CNX-774 | 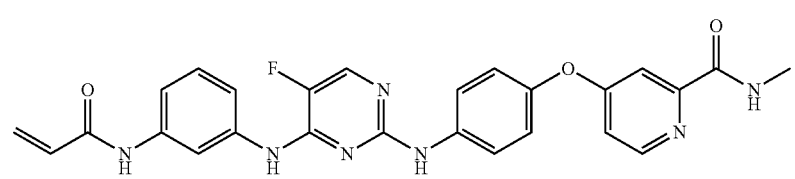 [SMILES: C=CC(=O)Nc1cccc(Nc2nc(Nc3ccc(Oc4ccnc(C(=O)NC)c4)cc3)ncc2F)c1] |
| 7 | XL388 | 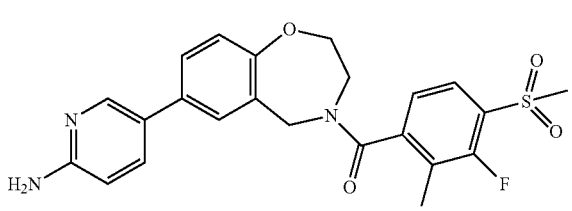 [SMILES: Cc1c(C(=O)N2CCOc3ccc(-c4ccc(N)nc4)cc3C2)ccc(S(C)(=O)=O)c1F] |

TABLE 3-continued
| Entry | Compound Name | Structure |
|---|---|---|
| 8 | GDC-0349 | 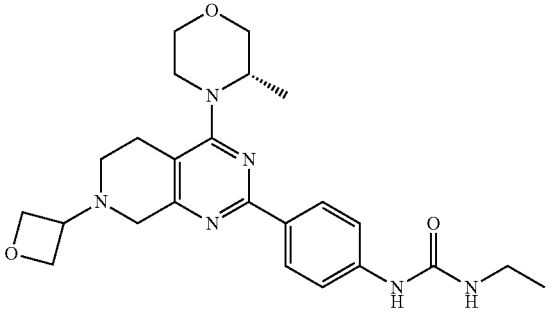 [SMILES: CCNC(=O)Nc1ccc(-c2nc3c(c(N4CCOC[C@@H]4C)n2)CCN(C2COC2)C3)cc1] |
| 9 | AZD2014 (vistusertib) | 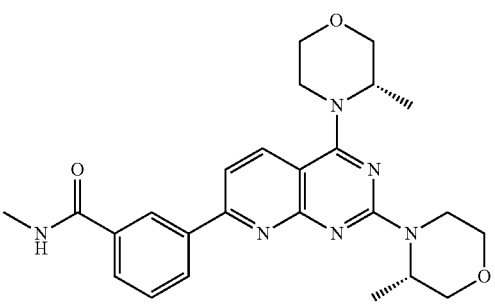 [SMILES: CNC(=O)c1cccc(-c2ccc3c(N4CCOC[C@@H]4C)nc(N4CCOC[C@@H]4C)nc3n2)c1] |
| 10 | AZD8055 | 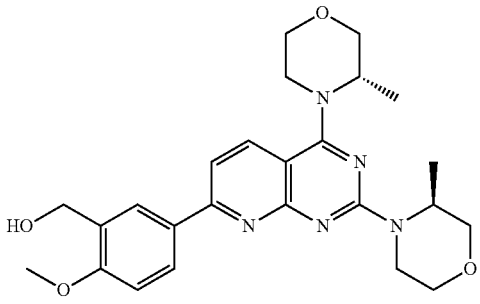 [SMILES: COc1ccc(-c2ccc3c(N4CCOC[C@@H]4C)nc(N4CCOC[C@@H]4C)nc3n2)cc1CO] |
| 11 | MLN0128 (sapanisertib) | 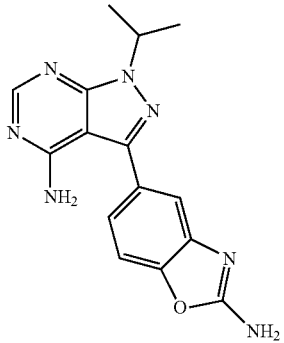 [SMILES: CC(C)n1nc(-c2ccc3oc(N)nc3c2)c2c(N)ncnc21] |
| 12 | CC-122 | 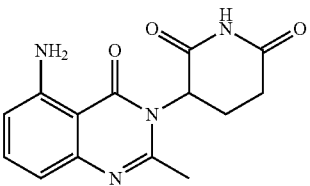 [SMILES: Cc1nc2cccc(N)c2c(=O)n1C1CCC(=O)NC1=O] |

TABLE 3-continued
| Entry | Compound Name | Structure |
|---|---|---|
| 13 | CC-220 | 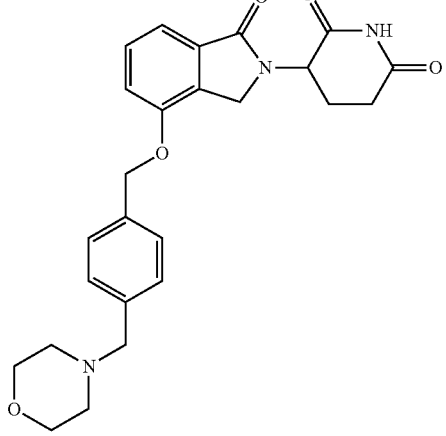 |
| 14 | PF-05212384 (gedatolisib) | 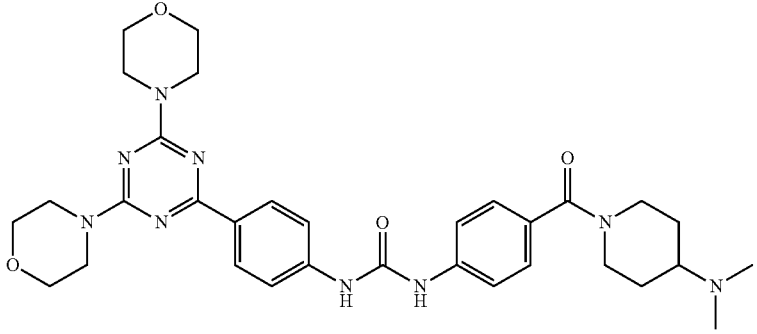 [SMILES: CN(C)C1CCN(C(=O)c2ccc(NC(=O)Nc3ccc(-c4nc(N5CCOCC5)nc(N5CCOCC5)n4)cc3)cc2)CC1] |
| 15 | GDC-0980 (pitolisib) | 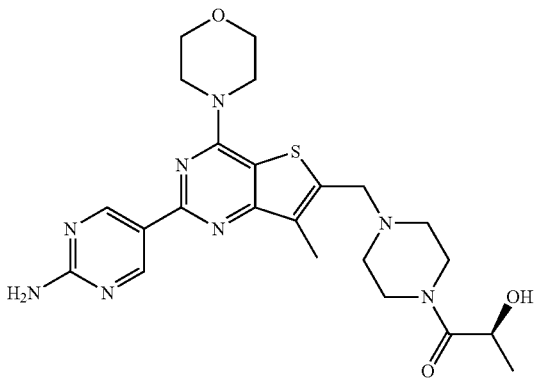 [SMILES: Cc1c(CN2CCN(C(=O)[C@H](C)O)CC2)sc2c(N3CCOCC3)nc(-c3cnc(N)nc3)nc12] |

TABLE 3-continued
| Entry | Compound Name | Structure |
|---|---|---|
| 16 | GSK2126458 | 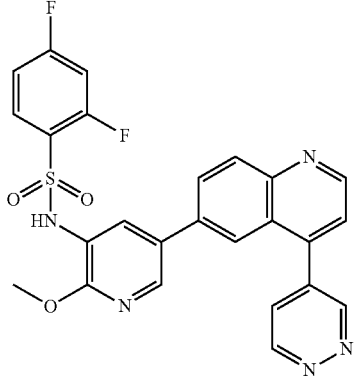 [SMILES: COc1ncc(-c2ccc3nccc(-c4ccnnc4)c3c2)cc1NS(=O)(=O)c1ccc(F)cc1F] |
| 17 | BEZ235 | 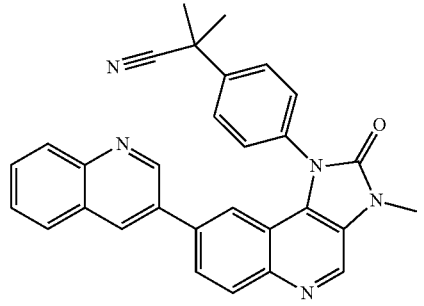 [SMILES: Cn1c(=O)n(-c2ccc(C(C)(C)C#N)cc2)c2c3cc(-c4cnc5ccccc5c4)ccc3ncc21] |
| 18 | IPI-145 (duvelisib) | 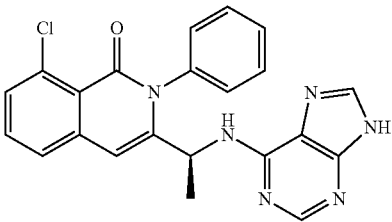 [SMILES: C[C@H](Nc1ncnc2[nH]cnc12)c1cc2cccc(Cl)c2c(=O)n1-c1ccccc1] |
| 19 | CAL-101 (idelalisib) | 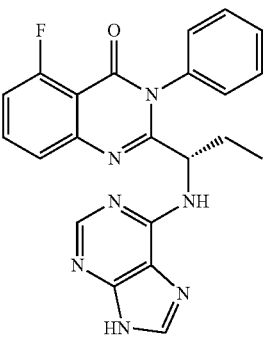 [SMILES: CC[C@H](Nc1ncnc2[nH]cnc12)c1nc2cccc(F)c2c(=O)n1-c1ccccc1] |

TABLE 3-continued
| Entry | Compound Name | Structure |
|---|---|---|
| 20 | ABT-199 (venetoclax) | 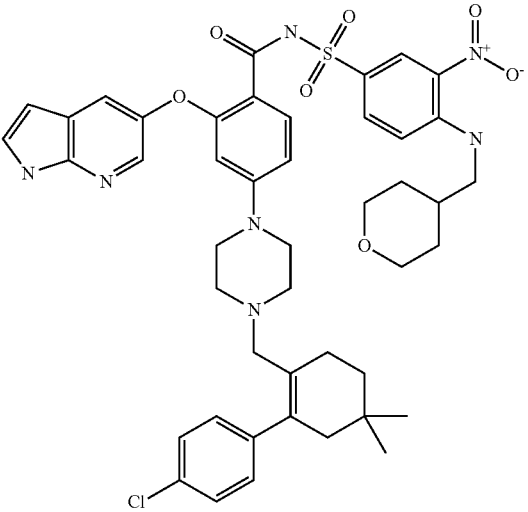 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1] |
| 21 | BI-97C1 (sabutoclax) | 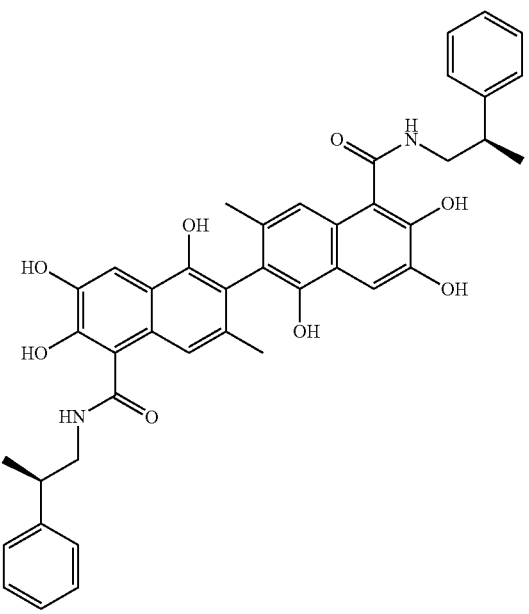 [SMILES: Cc1cc2c(C(=O)NC[C@H](C)c3ccccc3)c(O)c(O)cc2c(O)c1-c1c(C)cc2c(C(=O)NC[C@H](C)c3ccccc3)c(O)c(O)cc2c1O] |
| 22 | OTS964 | 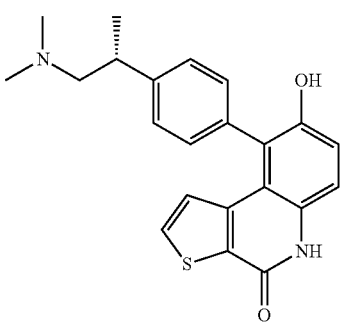 [SMILES: C[C@@H](CN(C)C)c1ccc(-c2c(O)ccc3[nH]c(=O)c4sccc4c23)cc1] |

TABLE 3-continued
| Entry | Compound Name | Structure |
|---|---|---|
| 23 | CH5424802 (alectinib) | 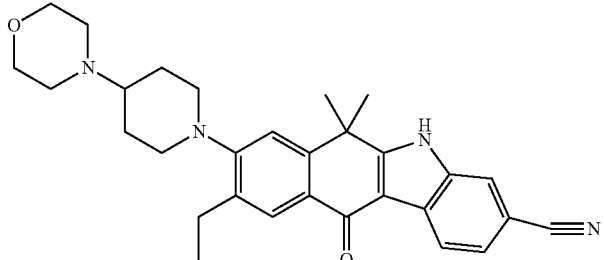 |
| 24 | PI-103 | 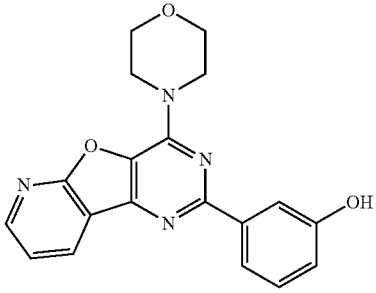 [SMILES: Oc1cccc(-c2nc(N3CCOCC3)c3oc4ncccc4c3n2)c1] |
| 25 | NVP-BEZ235 | 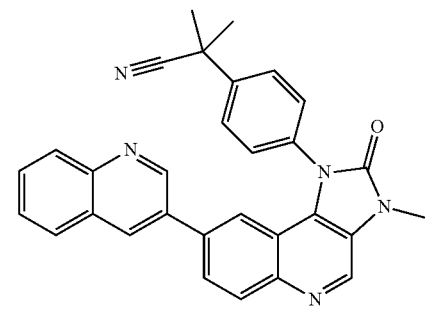 [SMILES: Cn1c(=O)n(-c2ccc(C(C)(C)C#N)cc2)c2c3cc(-c4cnc5ccccc5c4)ccc3ncc21] |
| 26 | WJD008 | 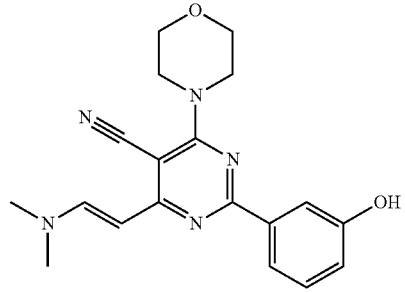 [SMILES: CN(C)/C=C/c1nc(-c2cccc(O)c2)nc(N2CCOCC2)c1C#N] |

TABLE 3-continued
| Entry | Compound Name | Structure |
|---|---|---|
| 27 | XL765 | 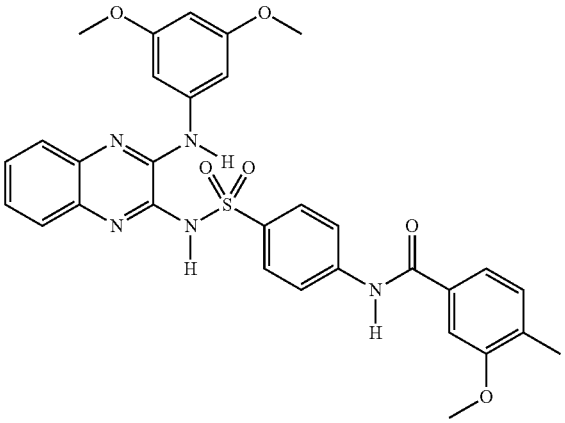 [SMILES: COc1cc(Nc2nc3ccccc3nc2NS(=O)(=O)c2ccc(NC(=O)c3ccc(C)c(OC)c3)cc2)cc(OC)c1] |
| 28 | SF-1126 | 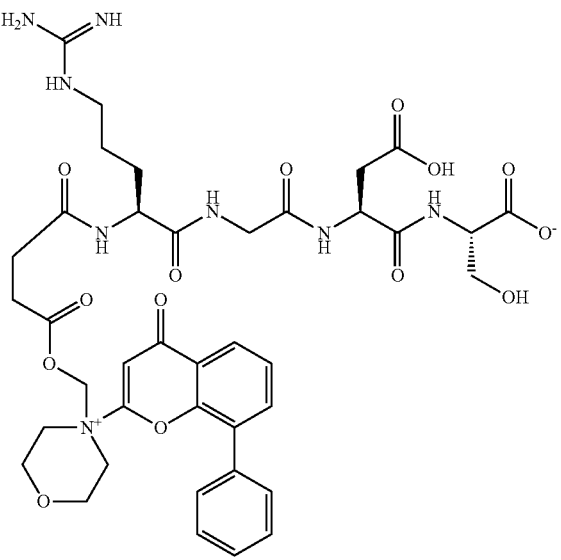 [SMILES: N=C(N)NCCC[C@H](NC(=O)CCC(=O)OC[N+]1(c2cc(=O)c3cccc(-c4ccccc4)c3o2)CCOCC1)C(=O)NCC(=O)N[C@@H](CC(=O)O)C(=O)N[C@@H](CO)C(=O)[O-]] |
| 29 | Torin1 | 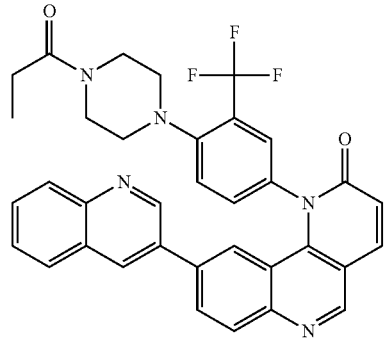 [SMILES: CCC(=O)N1CCN(c2ccc(-n3c(=O)ccc4cnc5ccc(-c6cnc7ccccc7c6)cc5c43)cc2C(F)(F)F)CC1] |

TABLE 3-continued
| Entry | Compound Name | Structure |
|---|---|---|
| 30 | PP242 | 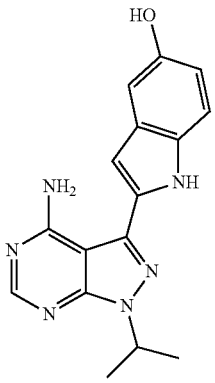 [SMILES: CC(C)n1nc(-c2cc3cc(O)ccc3[nH]2)c2c(N)ncnc21] |
| 31 | PP30 | 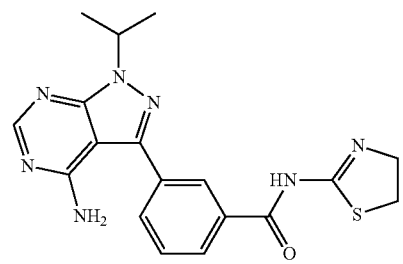 [SMILES: CC(C)n1nc(-c2cccc(C(=O)NC3=NCCS3)c2)c2c(N)ncnc21] |
| 32 | Ku-0063794 | 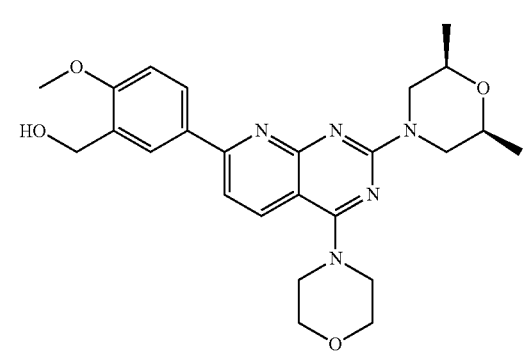 [SMILES: COc1ccc(-c2ccc3c(N4CCOCC4)nc(N4C[C@@H](C)O[C@@H](C)C4)nc3n2)cc1CO] |
| 33 | WYE-354 | 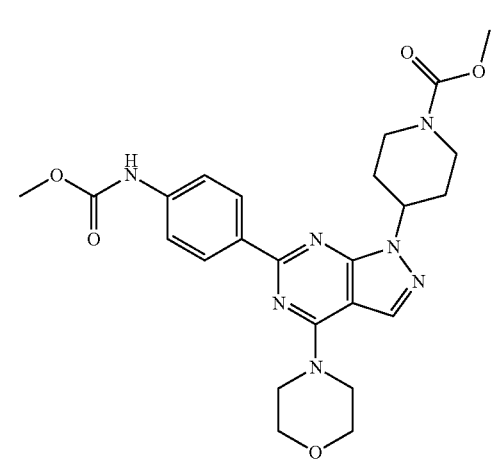 |

TABLE 3-continued
| Entry | Compound Name | Structure |
|---|---|---|
| 34 | WYE-687 | 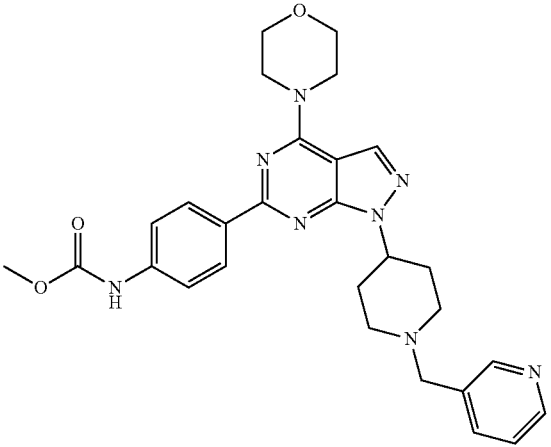 [SMILES: COC(=O)Nc1ccc(-c2nc(N3CCOCC3)c3cnn(C4CCN(Cc5cccnc5)CC4)c3n2)cc1] |
| 35 | WAY-600 | 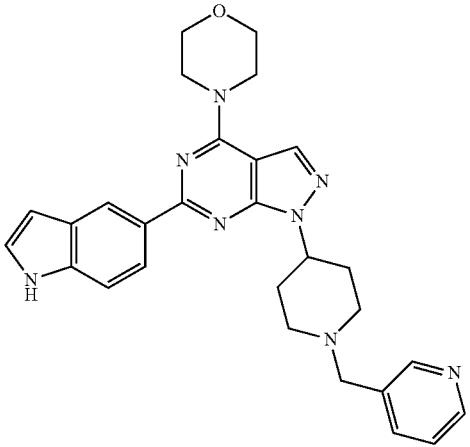 [SMILES: c1cncc(CN2CCC(n3ncc4c(N5CCOCC5)nc(-c5ccc6[nH]ccc6c5)nc43)CC2)c1] |
| 36 | INK128 | 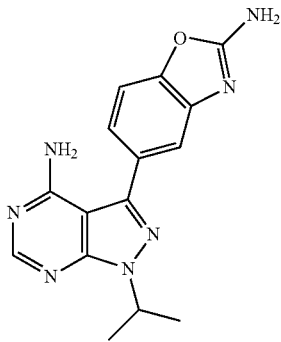 [SMILES: CC(C)n1nc(-c2ccc3oc(N)nc3c2)c2c(N)ncnc21] |

TABLE 3-continued
| Entry | Compound Name | Structure |
|---|---|---|
| 37 | OSI 027 | 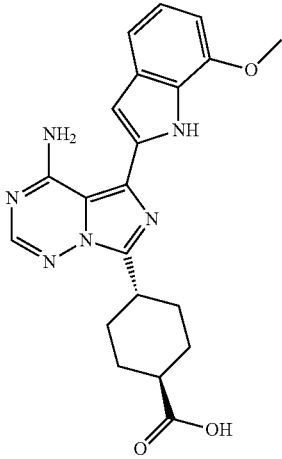 [SMILES: COc1cccc2cc(-c3nc([C@H]4CC[C@H](C(=O)O)CC4)n4ncnc(N)c34)[nH]c12] |
| 38 | CC-223 | 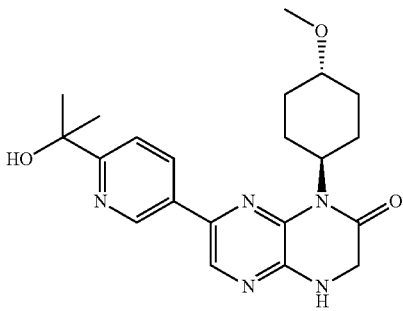 [SMILES: CO[C@H]1CC[C@H](N2C(=O)CNc3ncc(-c4ccc(C(C)(C)O)nc4)nc32)CC1] |
| 39 | LY3023414 | 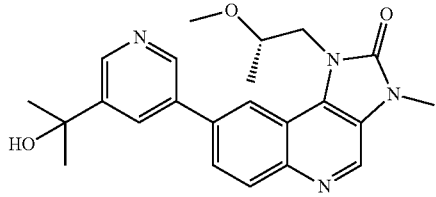 [SMILES: CO[C@@H](C)Cn1c(=O)n(C)c2cnc3ccc(-c4cncc(C(C)(C)O)c4)cc3c21] |
| 40 | PQR309 (bimiralisib) | 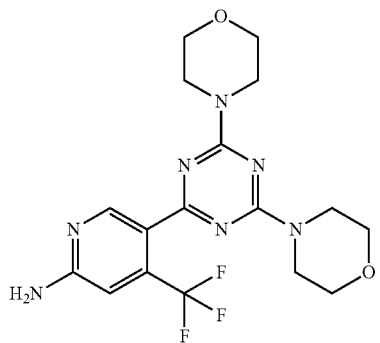 [SMILES: Nc1cc(C(F)(F)F)c(-c2nc(N3CCOCC3)nc(N3CCOCC3)n2)cn1] |

TABLE 3-continued

| Entry | Compound Name | Structure |
|---|---|---|
| 41 | SAR245409 (voxtalisib) | 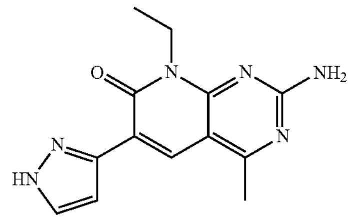 [SMILES: CCn1c(=O)c(-c2cc[nH]n2)cc2c(C)nc(N)nc21] |

Pharmaceutical Compositions

Pharmaceutical compositions comprising individual BTK inhibitor, mTOR inhibitor, IMiD, or the therapeutic monoclonal antibody or its derivative, or their combinations may be prepared using carriers, excipients and other appropriate additives. The administration forms may be oral dosage forms for the BTK inhibitor, mTOR inhibitor, and IMiD, such as tablets, pills, capsules, granules, powders, emulsions, syrups, suspensions, liquid preparations; or non-oral dosage forms, such as forms for intravenous, subcutaneous or intramuscular injection, suppository, transdermal implant, or inhalation.

Solid compositions for oral administration may be tablets, capsules, powders, granules and the like. In such solid compositions, one or more active substances with at least one inert excipient (e.g., lactose, mannitol, glucose, hydroxypropylcellulose, microcrystalline cellulose, starch, poly vinyl pyrrolidone, magnesium aluminum silicate, and the like) can be mixed. The compositions may contain inert additives such as lubricants (e.g. magnesium stearate), disintegrating agents (e.g., sodium carboxymethyl starch) and dissolution aids. If necessary, tablets or pills may be coated with appropriate coatings such as a sugar coating or a gastric or enteric coating agent.

The liquid compositions for oral administration include pharmaceutically acceptable emulsions, solutions, aqueous or oily suspensions, syrups, elixirs, and commonly used inert diluent (e.g., purified water, and ethanol). In addition to the inert diluent, the composition may also contain additives such as solubilizing agents, wetting agents, suspending agents, and sweetener, flavoring agents, flavoring agents and preservatives.

Injections for parenteral administration may include sterile aqueous or non-aqueous liquid preparations, suspensions, and emulsions. Diluent aqueous solutions may include distilled water and physiological saline. Non-aqueous diluent solutions may include propylene glycol, polyethylene glycol, vegetable oils, alcohols (e.g., ethanol), and polysorbate 80. Such compositions may further contain isotonic agents, such as preservatives, wetting agents, emulsifying agents, dispersing agents, stabilizing agents, dissolving aids and the like. The compositions can be sterilized by filtration through a bacteria retaining filter, addition of bactericides, or irradiation. In addition, these compositions may be made as sterile solid compositions and dissolved or suspended in sterile water or a sterile solvent for injection prior to use.

Pharmaceutical compositions used for transmucosal administration such as inhalation and nasal absorption can be solid, liquid, or semi-solid state of use, and can be made in accordance with conventional methods. For example, excipients such as lactose, starch, pH adjusting agents, preservatives, surfactants, lubricants, stabilizing and thickening agents and the like can be added. A suitable inhalation or insufflation device can be used. For example, metered dose inhaler devices may be used. A pressurized aerosol spray can also be used with a suitable propellant (e.g., chlorofluoroalkane, hydrofluoroalkane, or a suitable gas such as carbon dioxide).

In some embodiments, the therapeutic agents of the combination therapy of the present disclosure may be co-formulated into a single capsule or tablet. For example, for the BTK/mTOR doublet combination using Compound A and everolimus, 100 mg of Compound A and 1.25 mg of everolimus may be co-formulated into a single tablet or capsule, where the patient may be given one tablet (100 mg Compound A and 1.25 mg everolimus), two tablets (200 mg Compound A and 2.5 mg everolimus), or three tablets (300 mg Compound A and 3.75 mg everolimus) orally on a treatment day. In some embodiments, the single tablet or capsule further comprises 0.33, 0.5, or 0.67 mg pomalidomide.

In some embodiments, the BTK monotherapy or the combination therapies of the present disclosure are used as a first line therapy, to treat patients who have not been treated by another drug for the same condition. In other embodiments, the BTK monotherapy or the combination therapies of this invention are used as a second, third, or fourth line therapy, where the patients have been treated for the same condition unsuccessfully (e.g., refractory or relapsed) by another drug, for example, rituximab (which targets CD20 on B cells), CHOP (the cyclophosphamide-hydroxydaunorubicin-oncovin-prednisone therapy), or rituximab plus CHOP (R-CHOP).

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art.

Throughout this specification and embodiments, the word "comprise," or variations such as "comprises" or "comprising" will be understood to imply the inclusion of a stated integer or group of integers but not the exclusion of any other integer or group of integers. The materials, methods, and examples are illustrative only and not intended to be limiting.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. For example, the terms can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

The following examples are meant to illustrate the methods and materials of the present invention. Suitable modifications and adaptations of the described conditions and parameters normally encountered in the art which are obvious to those skilled in the art are within the spirit and scope of the present invention.

EXAMPLES

Example 1: Clinical Studies of Compound A Monotherapy for Relapsed/Refractory B-Cell Lymphomas and CLL This Example describes a Phase I, open-label clinical trials for evaluating the safety and tolerability of multiple dose oral administration of Compound A capsules in patients with B-cell lymphomas. The pharmacokinetics of Compound A was also evaluated.

Methods

Patient Enrollment

Patients who met the following inclusion criteria were enrolled in the trials in China: i) age≥18 years, no gender limits, and provide the informed consent form; ii) B-cell lymphoma classification is based on WHO classified definition, including CLL, small lymphocytic lymphoma (SLL); CLL with 17p-; MCL; WM; DLBCL, etc.; iii) measurable lesion: NHL requires at least one≥2 cm two-dimensional lesion diameter, CLL≥5000 leukemia cells/mm$^3$, WM IgM≥1000 mg/dL, bone marrow lymph plasma-like cells infiltration, histopathologically diagnosed as DLBCL; iv) patients failed in lymphoma treatment at least once and have no standard therapeutic options; DLBCL patients who are not suitable for or reject autologous stem cell transplantation; and v) ECOG (Eastern Cooperative Oncology Group) performance status 0~1. Meanwhile, patients who met any one of the following criteria were excluded: i) disease with changes of pathological tissue types (including large cell transformation); ii) patients received other BTK inhibitor therapy (China only); and iii) patients with HIV infection, or HBs-Ag or HBc-Ab positive.

Eligibility criteria for the U.S. study were similar to the China study, but histological subtypes included patients with relapsed/refractory CLL, Hodgkin lymphoma and B-cell NHL including DLBCL. Patients who had prior exposure to BTK inhibiting agents were permitted in the trial.

Study Design

Relapsed/refractory B-cell lymphoma patients who met the aforementioned enrollment criteria were enrolled without randomization. For the China trial, the study was conducted with escalating doses of Compound A monotherapy from 50 mg, 100 mg, 200 mg, to 400 mg daily. The patients were required to stay in the hospital for 24 hours after the first dosing. Compound A was orally administered for 28 days, with a one week follow up (35 day cycle). The standard 3+3 dose-escalation method was used (Eisenhauer et al., J Clin Oncol 18(3):684-92 (2000)): three patients were treated at the cohort dose level, and if no patient was observed to have dose-limiting toxicity (DLT) within one week after completing the Compound A course administration, the dose level was escalated one step for the next three patients. No intrapatient dose escalation of Compound A was permitted. To eliminate the occurrence of accidental or acute toxicity, the first patient receiving Compound A in each group was required to stay in the hospital for 24 hours after the first administration, and other patients were not allowed to receive Compound A during this period. The first 28 days of treatment was considered DLT period. Patients were permitted to continue Compound A treatment if the investigators determined that continued Compound A treatment would benefit the patients until the following scenario occurred: i) disease progression or unacceptable toxicity, or ii) the patients withdrew from the study.

The U.S. trial was a Phase Ia/Ib, first-in-human multi-center trial exploring Compound A as monotherapy or in combination with everolimus and pomalidomide in patients with relapsed/refractory CLL, Hodgkin lymphoma and B-cell NHL including DLBCL. Phase Ia was reported and consisted of escalating Compound A monotherapy doses of 50, 100, 200 mg and 300 mg. Compound A treatment was administered for 21 consecutive days of a 28-day cycle, until disease progression or unacceptable toxicity. The 50 mg and 100 mg cohorts were single patient cohorts that required an expanded number of patients in the case of Grade 2 or greater drug-related adverse events. Studies on the 200 mg and 300 mg cohorts were conducted in a standard 3+3 design.

Outcomes Assessment

The primary objective was to evaluate the safety and tolerability of multiple dose oral administration of Compound A capsules in patients with relapsed/refractory B-cell lymphomas. The response rate, including the partial response and complete response rate, was defined according to the Revised International Working Group Criteria for non-Hodgkin's lymphoma (Cheson et al., J Clin Oncol 25:579-86 (2007)). Drug-related adverse events (AEs), including DLT, non-hematologic AEs and hematologic AEs were recorded. The secondary objective was to evaluate the PK of multiple dose oral administration of Compound A capsules. The PK indexes of single dose administration included AUClast, AUC0-∞, Cmax, tmax, t1/2, CL/F and Vd/F. The PK indexes of steady state under continuous administration included AUCss, Cmax,ss and tmax,ss.

Statistical Analysis

The final sample size of the trials depended on the number of dose levels explored during the dose escalation phase. In order to assess the dosing regimens of Compound A capsules as monotherapy in a Phase Ia study, 5 to 11 patients were expected to be recruited. The data was analyzed according to the criteria agreed by the sponsor. All patients who received Compound A capsules were included in the assessment of the safety and tolerability of Compound A. All patients who received Compound A capsules and had PK data were used to assess the PK characteristics of Compound A. Other evaluable parameters were listed in the statistical report.

Results

Patients and Treatment

Thirteen patients (nine male and four female) who met the aforementioned inclusion/exclusion criteria were enrolled in China. There were seven patients with follicular lymphoma (FL), three patients with Waldenström's macroglobulinemia (WM), two patients with marginal zone B-cell lymphoma (MZL) and one patient with small lymphocytic lymphoma (SLL)/chronic lymphocytic leukemia (CLL). The median age of these patients was 56 years (range, 30 to 72 years). The median prior treatments were two (range, 1 to 6). Four patients were enrolled in the 50 mg dose cohort and three patients in each of the other three dose cohorts (100/200/400 mg). The detailed information is described in Table 4.

TABLE 4

Patient Characteristics at Baseline

| Characteristics | n | Percentage |
|---|---|---|
| Gender | | |
| Male | 9 | 69 |
| Female | 4 | 31 |
| Age, years | | |
| Median (range) | 56 (30-72) | |
| <50 | 9 | 69 |
| 50 | 4 | 31 |
| ECOG performance status | | |
| 0 | 13 | 100 |
| 1 | 0 | 0 |
| Pathology | | |
| FL | 7 | 54 |
| WM | 3 | 23 |
| MZL | 2 | 15 |
| SLL/CLL | 1 | 8 |
| No. of prior regimens | | |
| Median (range) | 2 (1-5) | |
| ≥3-no. (%) | 3 | 23 |

Five patients (three male and two female) were enrolled in the United States, including three with B-cell lymphomas, including one DLBCL and one marginal zone lymphoma, and two patients with CLL. One patient was treated in each of the 50 mg and 100 mg dose cohorts and three patients in the 200 mg dose cohort. The median age was 67 years (range, 46 to 77), and the median prior treatments were 2 (range, 1 to 5).

Safety Assessment

Among patients treated in China on the 28 day dosing schedule, the majority of drug-related AEs observed were grade 1. The most common hematologic AEs occurring in more than 20% of patients were leucopenia (23.1%), anemia (23.1%), and neutropenia (23.1%). Three patients experienced Grade 1 leucopenia, and three patients experienced Grade 1 anemia. One patient (7.7%) experienced Grade 1 neutropenia, and two patients (15.4%) experienced Grade 3 neutropenia. No Grade 2, 4 or 5 hematologic events occurred. Non-hematologic events included Grade 1 alanine aminotransferase (ALT) elevation events and Grade 3 pneumonia which occurred in one patient each (7.7%). No Grade 2, 4 or 5 non-hematologic events occurred. No dose-limiting toxicity occurred. Only one patient discontinued treatment for disease progression.

Among the five patients treated in the United States on the 21 day dosing schedule, adverse events were mostly Grade 1 and 2. Hematologic events included anemia (60%) and single patient events of Grade 3 thrombocytopenia and Grade 3 neutropenia. Non-hematologic events included upper respiratory infection (40%), contusion (40%) and arthralgia (40%) and single patient events of Grade 3 lung infection, bronchitis, myalgia, nausea, fatigue and purpura (all Grade 1). No patient discontinued study treatment due to AEs and no patient died on-study or within the 30-day follow-up period.

Efficacy Assessment

In the China trial, one patient voluntarily withdrew during the treatment and three FL patients experienced progressive disease after treatment. Therefore, nine patients (WM=3, FL=3, MZL=2, SLL/CLL=1) continued to receive Compound A beyond the first cycle. The median follow-up was 4.8 months (range, 1.6 to 10.5 months) as of September 2017. Among these patients, six patients were evaluated for response: WM (N=2: 2PR), FL (N=2: 1PR, 1SD), and MZL (N=2: 1CR, 1SD). PR: partial response; SD: stable disease; CR: complete response.

In the U.S. trial, three patients came off the study for disease progression after five months (B-cell lymphoma, 50 mg), 8 months (CLL, 200 mg) and 2 months (DLBCL, 200 mg) of Compound A monotherapy, respectively. Two patients continued treatment on study with Compound A monotherapy at 13 months (CLL, 100 mg) and 11 months (MZL). All patients were evaluated for response: CLL (N=2, 1PR, 1SD), MZL (1PR), B-cell lymphoma (1SD) and DLBCL (PD). PD: disease progression.

Tables 5A and 5B show the PK data of Compound A in the China trial on Day 1 and Day 8 of the treatment, respectively.

TABLE 5A

Compound A Plasma Levels (ng/mL) on Day 1 from the China Trial

| Pt | Dose | 0 h | 0.5 h | 1 h | 2 h | 4 h | 6 h | 24 h |
|---|---|---|---|---|---|---|---|---|
| 1 | 50 mg | 0 | 0 | 0 | 0 | 1.47 | 2.24 | 0 |
| 2 | 50 mg | 0 | 62.3 | 71.3 | 75.4 | 36.8 | 16.9 | 0 |
| 3 | 50 mg | 0 | 8.77 | 165 | 89.5 | 19.8 | 8.42 | 0 |
| 4 | 50 mg | 0 | 31.5 | 79.6 | 105 | 53.5 | 15 | 0 |
| 5 | 100 mg | 0 | 3.38 | 41.2 | 150 | 75.7 | 29.4 | 1.54 |
| 6 | 100 mg | 0 | 16.2 | 223 | 192 | 60 | 29.1 | 1.32 |
| 7 | 100 mg | 0 | 40.4 | 101 | 107 | 29.3 | 22.8 | 3 |
| 8 | 200 mg | 0 | 195 | 325 | 531 | 302 | 169 | 7.21 |
| 9 | 200 mg | 0 | 24.4 | 481 | 438 | 84.5 | 38.4 | 2.84 |

TABLE 5A-continued

Compound A Plasma Levels (ng/mL) on Day 1 from the China Trial

| Pt | Dose | 0 h | 0.5 h | 1 h | 2 h | 4 h | 6 h | 24 h |
|---|---|---|---|---|---|---|---|---|
| 10 | 200 mg | 0 | 237 | 182 | 125 | 94.1 | 44.5 | 6.89 |
| 11 | 400 mg | 0 | 16.4 | 520 | 407 | 134 | 85.9 | 4.15 |
| 12 | 400 mg | 0 | 969 | 1690 | 1300 | 243 | 107 | 16.9 |
| 13 | 400 mg | 0 | 23.7 | 207 | 190 | 184 | 130 | 12.5 |

TABLE 5B

Compound A Plasma Levels (ng/mL) on Day 8 from the China Trial

| Pt | Dose | 0 h | 0.5 h | 1 h | 2 h | 4 h | 6 h | 24 h |
|---|---|---|---|---|---|---|---|---|
| 1 | 50 mg | 0 | 3.78 | 25.3 | 17.7 | 10.7 | 0 | 0 |
| 3 | 50 mg | 1.48 | 4.6 | 21.1 | 157 | 36.3 | 11.4 | 0 |
| 4 | 50 mg | 0 | 32.0 | 67.6 | 51.5 | 23.8 | 6.74 | 0 |
| 5 | 100 mg | 1.06 | 45.2 | 198 | 83.0 | 37.7 | 15.5 | 1.27 |
| 6 | 100 mg | 1.25 | 67.9 | 149 | 166 | 72.1 | 32.6 | 1.34 |
| 7 | 100 mg | 2.22 | 3.73 | 51.3 | 135 | 87.7 | 40.7 | 1.73 |
| 8 | 200 mg | 3.69 | 125 | 369 | 537 | 293 | 165 | 7.23 |
| 9 | 200 mg | 5.13 | 90.8 | 239 | 273 | 127 | 50.9 | 1.91 |
| 10 | 200 mg | 3.53 | 279 | 369 | 295 | 104 | 53.1 | 3.51 |
| 11 | 400 mg | 4.68 | 29.9 | 499 | 417 | 159 | 61.4 | 2.65 |
| 12 | 400 mg | 50 | 613 | 468 | 289 | 214 | 133 | 49 |
| 13 | 400 mg | 11.0 | 6.54 | 62.4 | 108 | 217 | 161 | 5.94 |

Table 6 shows the PK data of Compound A in the U.S. trial on Day 1.

TABLE 6

Compound A Plasma Level (ng/mL) on Day 1 from the U.S. Trial

| Pt | Dose | 0 h | 0.5 h | 1 h | 2 h | 4 h | 6 h | 24 h |
|---|---|---|---|---|---|---|---|---|
| 1 | 50 mg | 0 | 2.84 | 26.9 | 63.4 | 15.3 | 6.44 | 0 |
| 2 | 100 mg | 9.04 | 44.9 | 53.3 | 21.3 | 13.3 | 13.3 | 3.06 |
| 3 | 200 mg | 0 | 0 | 93.5 | 144 | 43.9 | 19.6 | 3.39 |
| 4 | 200 mg | 0 | 0 | 4.91 | 62.2 | 149 | 40.9 | 1.07 |
| 5 | 200 mg | 0 | 0 | 9.23 | 86.5 | 101 | 84.6 | 17.2 |

Three additional patients were given 300 mg Compound A in the U.S. trial. The data show that Compound A was well tolerated in these patients as well at 300 mg.

The PK data demonstrate adequate exposures to Compound A in all patients at all of the dose levels.

These above data demonstrate that Compound A was safe and well tolerated in patients with relapsed/refractory CLL and B-cell lymphomas. The maximum tolerated dose had not been reached for the Compound A monotherapy. Patients in the China and U.S. trials had tolerated up to 23 more cycles of Compound A monotherapy. Meanwhile, preliminary efficacy was observed in WM, MZL, and SLL/CLL patients. The favorable toxicity profile indicates that Compound A can provide the opportunity for treating relapsed/refractory B-cell lymphomas with less intensive and equally or more effective regimens than those currently available.

Example 2: Treatment of B Cell Malignancies with Compound A/Everolimus Combination Therapy This Example describes a treatment regimen for patients with B cell malignancies with a combination of oral administration of Compound A and a low dose of everolimus. Compound A and everolimus are administered PO to patients with B cell malignancies at the daily doses shown in Table 7 below.

TABLE 7

Dosages for Compound A/Everolimus Combination Therapy

| Cohort | Compound A (mg) | Everolimus (mg) |
|---|---|---|
| 1 | 200 | 5 |
| 2 | 300 | 5 |
| 3 | 400 | 5 |
| 4 | 100 | 2.5 |
| 5 | 200 | 2.5 |
| 6 | 300 | 2.5 |

The drugs are administered for 14 consecutive days in a 21-day cycle, or 21 consecutive days in a 28-day cycle. Alternatively, the drugs are administered for 28 consecutive days in a 35-day cycle. The drugs may also be administered continuously (e.g., 28 consecutive days in a 28-day cycle). Multiple cycles may be administered until the patient reaches a desired clinical endpoint, or until disease progression or unacceptable toxicity occurs. B cell malignancies treated include CLL and non-Hodgkin B-cell lymphomas, such as small lymphocytic lymphoma (SLL), follicular lymphoma (FL), diffuse large B-cell lymphoma (DLBCL), Waldenström's Macroglobulinemia (WM), marginal zone lymphoma (MZL), and mantle cell lymphoma (MCL). The B cell malignancies may be advanced, relapsed or refractory. It is expected that these combination therapies will benefit the patients by effectively reducing the tumor burden and volume with synthetic lethality to malignant cells and a favorable side effects profile.

Example 3: Treatment of B Cell Malignancies with Compound A/Everolimus/Pomalidomide Combination Therapy This example describes a treatment regimen for patients with B cell malignancies with a combination of oral administration of Compound A with low doses of everolimus and pomalidomide. The three drugs are administered PO to patients with B cell malignancies at the daily doses shown in Table 8 below.

TABLE 8

Dosages for Compound A/ Everolimus/Pomalidomide Combination Therapy

| Cohort | Compound A (mg) | Everolimus (mg) | Pomalidomide (mg) |
|---|---|---|---|
| 1 | 200 | 5 | 1 or 2 |
| 2 | 300 | 5 | 1 or 2 |
| 3 | 200 | 2.5 | 1 or 2 |
| 4 | 300 | 2.5 | 1 or 2 |

The drugs are administered for 21 consecutive days in a 28-day cycle. Alternatively, the drugs are administered for 14 consecutive days in a 21-day cycle. Multiple cycles may be administered until disease progression or unacceptable toxicity occurs. B cell malignancies treated include CLL and non-Hodgkin B-cell lymphomas, such as small lymphocytic lymphoma (SLL), follicular lymphoma (FL), diffuse large B-cell lymphoma (DLBCL), Waldenström's Macroglobulinemia (WM), marginal zone lymphoma (MZL), and mantle cell lymphoma (MCL). The B cell malignancies may be advanced, relapsed or refractory. It is expected that these combination therapies will benefit the patients by effectively reducing the tumor burden and volume with synthetic lethality to malignant cells and a favorable side effects profile.

Example 4: Treatment of B Cell Malignancies with Oral Compound A/Everolimus Doublet and Oral Compound A/Everolimus/Pomalidomide Triplet Therapies in Clinical Trials This Example describes a Phase I, open-label clinical trial for evaluating the safety and anti-tumor activity of the oral Compound A/everolimus doublet therapy and Compound A/everolimus/pomalidomide triplet therapy in patients with B-cell lymphoma using the "3+3" study design.

Methods

Eligible patients were at least 18 years old, having ECOG performance status less than 2 with relapsed/refractory chronic lymphocytic leukemia (CLL), diffuse large B-cell lymphoma (DLBCL), mantle cell lymphoma (MCL), follicular lymphoma (FL) or classical Hodgkin lymphoma (cHL). Study treatment was administered daily for 21 consecutive days over a 28-day cycle. The dose-limiting toxicity (DLT) period was defined during the first cycle of therapy, and treatment was continued until disease progression or unacceptable toxicity. Patients underwent tumor evaluations every 2 months and response was recorded using revised response criteria (IWCLL and Cheson 2014).

In the doublet therapy, Compound A and everolimus were administered PO to patients with B cell malignancies at the daily doses shown in Table 7 above.

In the triplet therapy, Compound A, everolimus, and pomalidomide were administered PO to patients with B cell malignancies at the daily doses shown in Table 8 above.

Results

Seven patients with DLBCL, CLL, MCL, FL and cHL were treated with the oral doublet therapy for 2 to 12 cycles. Table 9 shows the results of the oral doublet therapy.

TABLE 9

Results of Oral Doublet Therapy

| Patient ID | Subtype | Prior Therapies | Length of Therapy | Adverse Effects | Best response |
|---|---|---|---|---|---|
| 001 | DLBCL | 4 lines of therapy | 5 Cycles | Epistaxis (Grade 1); Stomatitis (Grade 1); Anemia (Grade 1); Abdominal pain (Grade 1) | PR |
| 002 | CLL | 2 lines of therapy | 7 Cycles | Leukopenia (Grade 1); Thrombocytopenia (Grade 1); Weight decreased (Grade 1); Neutropenia (Grade 2); Stomatitis (Grade 1) | PR |
| 003 | DLBCL | 3 lines of therapy | 5 Cycles | Transient pyrexia (Grade 1); Diarrhea (Grade 1) | PR, migrated from monotherapy |
| 004 | MCL | 3 lines of therapy | 3 Days off study due to existing AEs | Small intestinal obstruction | Off study, Surgery not study-drug-related |
| 005 | FL | 5 lines of therapy | 12 Cycles | Contusion (Grade 1); Dysgeusia (Grade 1) | PR, Migrated to Oral Triplet Therapy |
| 006 | cHL | 7 lines of therapy | 4 Cycles, On-going | Myalgia (Grade 1) | PR |
| 007 | CLL with Richter's transformation | 1 line of therapy | 2 Cycles On-going | Hyperphosphatemia (Grade 1); blurred vision (Grade 1); Thrombocytopenia (Grade 3) (rebound in the off-treatment week) | PR |

PR: Partial response.

Three patients (2 DLBCL, 1 FL) had been treated with the oral triplet therapy, including one patient transitioned from the doublet therapy. Table 10 shows the results of the oral triplet therapy.

TABLE 10

Results of Oral Triplet Therapy

| Patient ID | Subtype | Prior Therapies | Length of Therapy | Adverse Effects | Preliminary Assessment |
|---|---|---|---|---|---|
| 08 Previously on Oral Doublet Therapy | FL | 6 lines of therapy | 1 Cycle On-going | None observed | To be scheduled |
| 09 | DLBCL | 3 lines of therapy | 2 Cycles On-going | Thrombocytopenia (Grade 3, rebound in the off-treatment week); Rash (Grade 2) | PR |
| 10 | DLBCL | 1 line of therapy | 2 Cycles On-going | Thrombocytopenia (Grade 1, rebound in the off-treatment week); Rash (Grade 2) | PR |

Most AEs were known and manageable. Recurring AEs were mostly grade 1 or 2 and responses had been seen with both the oral doublet therapy and the oral triplet therapy across diverse lymphoma histologies (see Table 9 and Table 10). All patients evaluable for response demonstrated partial response (PR) to the oral doublet therapy and the oral triplet therapy, with 2/7 (doublet) and 3/3 (triplet) patients remaining on therapy.

The data above demonstrate that the maximum tolerated dose had not been reached for the current fixed dose doublet and triplet combinations. Toxicities had been mild and repeated cycles of study treatment had been well tolerated and manageable during subsequent treatment cycles.

The invention claimed is:

1. A method of treating a lymphoid malignancy in a human patient in need thereof, comprising administering to the patient Compound A, which is 1-((R)-3-(4-amino-3-(2-fluoro-4-(2,3,5,6-tetrafluorophenoxy)phenyl)-1H-pyrazolo[3,4-d]pyrimidin-1-yl)pyrrolidin-1-yl)prop-2-en-1-one, or an enantiomer, a diastereomer, a pharmaceutically acceptable salt, or a prodrug of Compound A, in one or more treatment cycles, wherein Compound A is administered to the patient at a daily dose of 50-400 mg for 14-28 treatment days in each treatment cycle.

2. The method of claim 1, wherein each treatment cycle is 21-35 days.

3. The method of claim 1, wherein Compound A is administered for
   (i) 14 treatment days every 21 days,
   (ii) 21 treatment days every 28 days,
   (iii) 28 treatment days every 28 days, or
   (iv) 28 treatment days every 35 days.

4. The method of claim 1, wherein the daily dose of Compound A is 50, 100, 150, 200, 300, or 400 mg.

5. The method of claim 1, wherein the lymphoid malignancy is a B-cell malignancy.

6. The method of claim 5, wherein the B-cell malignancy is a relapsed or refractory B-cell malignancy.

7. The method of claim 5, wherein the B-cell malignancy is B-cell lymphoma.

8. The method of claim 7, wherein the B-cell lymphoma is non-Hodgkin B-cell lymphoma.

9. The method of claim 8, wherein the non-Hodgkin B-cell lymphoma is selected from the group consisting of chronic lymphocytic leukemia, small lymphocytic lymphoma, follicular lymphoma, diffuse large B-cell lymphoma, Waldenström's Macroglobulinemia, marginal zone lymphoma, and mantle cell lymphoma.

10. The method of claim 1, wherein Compound A is administered in combination with a therapeutic monoclonal antibody or a derivative thereof, or with chimeric antigen receptor (CAR) T-cell therapy.

11. The method of claim 10, wherein the therapeutic monoclonal antibody or the CAR T-cell therapy targets a cell surface receptor on B cells, and wherein optionally the cell surface receptor is CD20, CD30, or CD52.

12. The method of claim 10, wherein Compound A is administered in combination with a therapeutic monoclonal antibody selected from the group consisting of rituximab, obinutuzumab, ofatumumab, ibritumomab tiuxetan, alemtuzumab, and brentuximab vedotin.

13. The method of claim 1, further comprising administering a therapeutically effective amount of a mammalian target of rapamycin (mTOR) inhibitor to the patient in said one or more treatment cycles.

14. The method of claim 13, wherein the mTOR inhibitor is everolimus, rapamycin, [7-(6-Amino-3-pyridinyl)-2,3-dihydro-1,4-benzoxazepin-4(5H)-yl][3-fluoro-2-methyl-4-(methylsulfonyl)phenyl]-methanone (XL388), N-ethyl-N'-[4-[5,6,7,8-tetrahydro-4-[(3S)-3-methyl-4-morpholinyl]-7-(3-oxetanyl)pyrido[3,4-d]pyrimidin-2-yl]phenyl]-Urea (GDC-0349), 3-(2,4-bis((S)-3-methylmorpholino)pyrido[2,3-d]pyrimidin-7-yl)-N-methylbenzamide (AZD2014), (5-(2,4-bis((S)-3-methylmorpholino)pyrido[2,3-d]pyrimidin-7-yl)-2-methoxyphenyl)methanol (AZD8055), GSK105965, 3-(2-aminobenzo[d]oxazol-5-yl)-1-isopropyl-1H-pyrazolo[3,4-d]pyrimidin-4-amine (TAK-228 or MLN0128), temsirolimus, ridaforolimus, PI-103, NVP-BEZ235, WJD008, XL765, SF-1126, Torin1, PP242, PP30, Ku-0063794, WYE-354, WYE-687, WAY-600, INK128, OSI 027, gedatolisib (PF-05212384), CC-223, LY3023414, PQR309, LXI-15029, SAR245409, or a pharmaceutically acceptable salt or a prodrug thereof.

15. The method of claim 13, wherein the mTOR inhibitor is everolimus and the method comprises administering everolimus to the patient at a daily dose of 0.5-25 mg on said treatment days.

16. The method of claim 15, wherein the daily dose of everolimus is 0.5, 1, 1.25, 1.5, 2.5, 3.75, or 5 mg.

17. The method of claim 13, further comprising administering a therapeutically effective amount of an immunomodulatory drug (IMiD) to the patient in said one or more treatment cycles.

18. The method of claim 17, wherein the IMiD is thalidomide, lenalidomide, pomalidomide, CC-112, CC-220, or a pharmaceutically acceptable salt or a prodrug thereof.

19. The method of claim 17, comprising administering pomalidomide to the patient at a daily dose of 0.2-4 mg.

20. The method of claim 19, wherein the daily dose of pomalidomide is 0.33, 0.5, 0.67, 1, 2, 3, or 4 mg.

21. The method of claim 1, comprising administering to the patient a tablet or capsule comprising (a) 200 mg of Compound A and (b) 5 mg of everolimus p.o. for
  (i) 14 treatment days in a 21-day treatment cycle,
  (ii) 21 treatment days in a 28-day treatment cycle,
  (iii) 28 treatment days in a 28-day treatment cycle, or
  (iv) 28 treatment days in a 35-day treatment cycle.

22. The method of claim 1, comprising administering to the patient a tablet or capsule comprising (a) 200 mg of Compound A, (b) 5 mg of everolimus, and (c) 2 mg of pomalidomide p.o. for
  (i) 14 treatment days in a 21-day treatment cycle,
  (ii) 21 treatment days in a 28-day treatment cycle, or
  (iii) 28 treatment days in a 28-day treatment cycle.

23. The method of claim 1, comprising administering to the patient two tablets or capsules, each comprising (a) 100 mg of Compound A, (b) 2.5 mg of everolimus, and (c) 1 mg of pomalidomide p.o. for
  (i) 14 treatment days in a 21-day treatment cycle,
  (ii) 21 treatment days in a 28-day treatment cycle, or
  (ii) 28 treatment days in a 28-day treatment cycle.

* * * * *

UNITED STATES PATENT AND TRADEMARK OFFICE
CERTIFICATE OF CORRECTION

PATENT NO. : 11,622,965 B2
APPLICATION NO. : 16/763483
DATED : April 11, 2023
INVENTOR(S) : Wei He Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 140 days.

Signed and Sealed this
Thirty-first Day of December, 2024

Derrick Brent
*Acting Director of the United States Patent and Trademark Office*